United States Patent [19]

Donovan

[11] Patent Number: 5,338,544
[45] Date of Patent: Aug. 16, 1994

[54] CRYIIB PROTEIN, INSECTICIDAL COMPOSITIONS AND METHODS OF USE THEREOF

[75] Inventor: William P. Donovan, Levittown, Pa.

[73] Assignee: Ecogen Inc., Del.

[21] Appl. No.: 23,736

[22] Filed: Feb. 26, 1993

Related U.S. Application Data

[60] Continuation of Ser. No. 751,452, Aug. 28, 1991, abandoned, which is a division of Ser. No. 379,015, Jul. 11, 1989, Pat. No. 5,073,632, which is a continuation-in-part of Ser. No. 39,542, Apr. 16, 1987, abandoned.

[51] Int. Cl.$^5$ ................. A01N 63/00; A01N 37/18
[52] U.S. Cl. .................. 424/93.2; 424/93.461; 435/69.1; 435/252.31; 514/2; 530/350
[58] Field of Search ............. 435/252.31, 172.3, 320.1, 435/69.1; 424/93 A, 93 L; 530/350, 825; 514/2

[56] References Cited

U.S. PATENT DOCUMENTS 4,713,241 12/1987 Wakisaka et al. ................. 424/93 L

FOREIGN PATENT DOCUMENTS 318143 5/1989 European Pat. Off. ..

OTHER PUBLICATIONS

Yamamoto, et al., "Isolation of a Protein from the Parasporal Crystal of *Bacillus thuringiensis* . . .", *Biochem. Biophys Res. Commun.* (1981) 103: 414–421.
Yamamoto, et al., "Two Types of Entomocidal Toxins in the Parasporal Cyrstals of *Bacillus thuringiensis kurstaki* ", *Arch. Biochem. Biophys.* (1983) 227: 233–241.
Thorne, et al., "Structural Similarity between the Lepidoptera-and Diptera-Specific Insecticidal Endotoxin Genes . . .", *J. Bacteriol.* 166: 801–811.
Mohamed, et al (1983) Environ Entomol 12: 1403–1405.
Wu et al., "Sequence of an operon containing a novel δ-endotoxin gene . . .", *FEMS Microbiol. Lett.* (1991) 81:31–36.
Nicholls et al., "Evidence of Two Different Types of Insecticidal P2 Toxins . . .", *J. Bacteriol.* (1989) 171:5141–5147.
Höfte et al., "Insecticidal Crystal Proteins of *Bacillus thuringiensis*", *Microbiol. Rev.* (1989) 53:252–255.
Widner et al., "Two Highly Related Insecticidal Crystal Proteins . . .", *J. Bacteriol.* (1989) 17:965–974.
Donovan et al., "Amino acid sequence and entomocidal activity of the P2 crystal protein . . .", *J. Biol. Chem.* (1989) 264:4740.
Donovan et al., "Amino Acid Sequence and Entomocidal Activity of the P2 Cyrstal Protein", *J. Biol. Chem.* (1988) 263:561–567.
Donovan et al., "Isolation and characterization of EG2158 . . .", *Mol. Gen. Genet.* (1988) 214:365–372.
Sekar, "The Insecticidal Crystal Protein Gene is Expressed . . .", *Curr. Microbiol.* (1988) 17:347–349.
Herrnstadt et al., "Nucleotide sequence and deduced amino acid sequence . . .", *Gene* (1987) 57:37–46.
Sekar et al., "Molecular cloning and characterization of the insecticidal crystal protein gene . . .", *Proc. Natl. Acad. Sci. USA* (1987) 84:7036–7040.
Höfte et al., "Nucleotide sequence of a gene encoding an insecticidal protein . . .", *Nucleic Acids Res.* (1987) 15:7183.
Zoller et al., "Oligonucleotide-Directed Mutagenesis . . .", *Methods Enzymol.* (1987) 154:329–350.
Kunkel et al., "Rapid and Efficient Site-Specific Mutagenesis . . .", *Methods Enzymol.* (1987) 154:367–382.
Aronson et al., "*Bacillus thuringiensis* and Related Insect Pathogens", *Microbiol. Rev.* (1986) 50:1–24.
Queen et al., "A comprehensive sequence analysis program . . .", *Nucleic Acids Res.* (1984) 12:581–599.
Sanger et al., "DNA sequencing with chain-terminating inhibitors", *Proc. Natl. Acad. Sci USA* (1977) 74:5463–5467.
Southern, "Detection of Specific Sequences Among DNA Fragments . . .", *J. Molec. Biol. (1975) 98:503–517.*
Daum, "Revision of Two Computer Programs for Probit Analysis", *Bull. Entomol. Soc. Am.* (1970) 16:10–15.

*Primary Examiner*—Che S. Chereskin
*Attorney, Agent, or Firm*—Christopher Egolf; Alan S. Nadel

[57] ABSTRACT

The present invention relates to a CryIIB protein which is insecticidal against lepidopteran insects, insecticidal compositions comprising the CryIIB protein and methods for use thereof.

6 Claims, 16 Drawing Sheets

Figure 2a

```
         10        20        30        40        50        60
GTATACACACAAGATTTAATTGATACGTATAATCAAAGTCAGAATTGTGATTGTGGTTGT
AccI 70        80        90       100       110       120
AAGTAGTAAGTAGTAAGTAGTTTCTTAAACATACTCGTTATTATCAAAAGAGTTTAGTTT 130       140       150       160       170       180
TAATATAAAACTAGATATTTAAGGAGGAATTTTATATGAATAATGTATTGAATAGTGGAA
                                      MetAsnAsnValLeuAsnSerGlyA 190       200       210       220       230       240
GAACAACTATTTGTGATGCGTATAATGTAGTAGCCCATGATCCATTTAGTTTTGAACATA
rgThrThrIleCysAspAlaTyrAsnValValAlaHisAspProPheSerPheGluHisL 250       260       270       280       290       300
AATCATTAGATACCATCCAAAAAGAATGGATGGAGTGGAAAAGAACAGATCATAGTTTAT
ysSerLeuAspThrIleGlnLysGluTrpMetGluTrpLysArgThrAspHisSerLeuT 310       320       330       340       350       360
ATGTAGCTCCTGTAGTCGGAACTGTGTCTAGTTTTTTGCTAAAGAAAGTGGGGAGTCTTA
yrValAlaProValValGlyThrValSerSerPheLeuLeuLysLysValGlySerLeuI 370       380       390       400       410       420
TTGGAAAAAGGATATTGAGTGAATTATGGGGATAATATTTCCTAGTGGTAGTACAAATC
leGlyLysArgIleLeuSerGluLeuTrpGlyIleIlePheProSerGlySerThrAsnL 430       440       450       460       470       480
TAATGCAAGATATTTTAAGGGAGACAGAACAATTCCTAAATCAAAGACTTAATACAGATA
euMetGlnAspIleLeuArgGluThrGluGlnPheLeuAsnGlnArgLeuAsnThrAspT 490       500       510       520       530       540
CCCTTGCTCGTGTAAATGCAGAATTGATAGGGCTCCAAGCGAATATAAGGGAGTTTAATC
hrLeuAlaArgValAsnAlaGluLeuIleGlyLeuGlnAlaAsnIleArgGluPheAsnG 550       560       570       580       590       600
AACAAGTAGATAATTTTTTAAACCCTACTCAAAACCCTGTTCCTTTATCAATAACTTCTT
lnGlnValAspAsnPheLeuAsnProThrGlnAsnProValProLeuSerIleThrSerS 610       620       630       640       650       660
CGGTTAATACAATGCAGCAATTATTTCTAAATAGATTACCCCAGTTCCAGATACAAGGAT
erValAsnThrMetGlnGlnLeuPheLeuAsnArgLeuProGlnPheGlnIleGlnGlyT 670       680       690       700       710       720
ACCAGTTGTTATTATTACCTTTATTTGCACAGGCAGCCAATATGCATCTTTCTTTTATTA
yrGlnLeuLeuLeuLeuProLeuPheAlaGlnAlaAlaAsnMetHisLeuSerPheIleA 730       740       750       760       770       780
GAGATGTTATTCTTAATGCAGATGAATGGGGTATTTCAGCAGCAACATTACGTACGTATC
rgAspValIleLeuAsnAlaAspGluTrpGlyIleSerAlaAlaThrLeuArgThrTyrA 790       800       810       820       830       840
GAGATTACCTGAGAAATTATACAAGAGATTATTCTAATTATTGTATAAATACGTATCAAA
rgAspTyrLeuArgAsnTyrThrArgAspTyrSerAsnTyrCysIleAsnThrTyrGlnT
```

Figure 2B

```
        850       860       870       880       890       900
CTGCGTTTAGAGGGTTAAACACCCGTTTACACGATATGTTAGAATTTAGAACATATATGT
hrAlaPheArgGlyLeuAsnThrArgLeuHisAspMetLeuGluPheArgThrTyrMetP 910       920       930       940       950       960
TTTTAAATGTATTTGAATATGTATCCATTTGGTCATTGTTTAAATATCAGAGTCTTATGG
heLeuAsnValPheGluTyrValSerIleTrpSerLeuPheLysTyrGlnSerLeuMetV 970       980       990      1000      1010      1020
TATCTTCTGGCGCTAATTTATATGCTAGCGGTAGTGGACCACAGCAGACACAATCATTTA
alSerSerGlyAlaAsnLeuTyrAlaSerGlySerGlyProGlnGlnThrGlnSerPheT 1030      1040      1050      1060      1070      1080
CAGCACAAAACTGGCCATTTTTATATTCTCTTTTCCAAGTTAATTCGAATTATATATTAT
hrAlaGlnAsnTrpProPheLeuTyrSerLeuPheGlnValAsnSerAsnTyrIleLeuS 1090      1100      1110      1120      1130      1140
CTGGTATTAGTGGTACTAGGCTTTCTATTACCTTCCCTAATATTGGTGGTTTACCGGGTA
erGlyIleSerGlyThrArgLeuSerIleThrPheProAsnIleGlyGlyLeuProGlyS 1150      1160      1170      1180      1190      1200
GTACTACAACTCATTCATTGAATAGTGCCAGGGTTAATTATAGCGGAGGAGTTTCATCTG
erThrThrThrHisSerLeuAsnSerAlaArgValAsnTyrSerGlyGlyValSerSerG 1210      1220      1230      1240      1250      1260
GTCTCATAGGGGCGACTAATCTCAATCACAACTTTAATTGCAGCACGGTCCTCCCTCCTT
lyLeuIleGlyAlaThrAsnLeuAsnHisAsnPheAsnCysSerThrValLeuProProL 1270      1280      1290      1300      1310      1320
TATCAACACCATTTGTTAGAAGTTGGCTGGATTCAGGTACAGATCGAGAGGGCGTTGCTA
euSerThrProPheValArgSerTrpLeuAspSerGlyThrAspArgGluGlyValAlaT 1330      1340      1350      1360      1370      1380
CCTCTACGAATTGGCAGACAGAATCCTTTCAAACAACTTTAAGTTTAAGGTGTGGTGCTT
hrSerThrAsnTrpGlnThrGluSerPheGlnThrThrLeuSerLeuArgCysGlyAlaP 1390      1400      1410      1420      1430      1440
TTTCAGCCCGTGGAAATTCAAACTATTTCCCAGATTATTTTATCCGTAATATTTCTGGGG
heSerAlaArgGlyAsnSerAsnTyrPheProAspTyrPheIleArgAsnIleSerGlyV 1450      1460      1470      1480      1490      1500
TTCCTTTAGTTATTAGAAACGAAGATCTAACAAGACCGTTACACTATAACCAAATAAGAA
alProLeuValIleArgAsnGluAspLeuThrArgProLeuHisTyrAsnGlnIleArgA 1510      1520      1530      1540      1550      1560
ATATAGAAAGTCCTTCGGGAACACCTGGTGGAGCACGGGCCTATTTGGTATCTGTGCATA
snIleGluSerProSerGlyThrProGlyGlyAlaArgAlaTyrLeuValSerValHisA 1570      1580      1590      1600      1610      1620
ACAGAAAAAATAATATCTATGCCGCTAATGAAAATGGTACTATGATCCATTTGGCGCCAG
snArgLysAsnAsnIleTyrAlaAlaAsnGluAsnGlyThrMetIleHisLeuAlaProG 1630      1640      1650      1660      1670      1680
AAGATTATACAGGATTTACTATATCGCCAATACATGCCACTCAAGTGAATAATCAAACTC
luAspTyrThrGlyPheThrIleSerProIleHisAlaThrGlnValAsnAsnGlnThrA
```

FIGURE 2C

```
      1690        1700       1710       1720       1730       1740
GAACATTTATTTCTGAAAAATTTGGAAATCAAGGTGATTCCTTAAGATTTGAACAAAGCA
  rgThrPheIleSerGluLysPheGlyAsnGlnGlyAspSerLeuArgPheGluGlnSerA 1750        1760       1770       1780       1790       1800
ACACGACAGCTCGTTATACGCTTAGAGGGAATGGAAATAGTTACAATCTTTATTTAAGAG
snThrThrAlaArgTyrThrLeuArgGlyAsnGlyAsnSerTyrAsnLeuTyrLeuArgV 1810        1820       1830       1840       1850       1860
TATCTTCAATAGGAAATTCAACTATTCGAGTTACTATAAACGGTAGAGTTTATACTGTTT
alSerSerIleGlyAsnSerThrIleArgValThrIleAsnGlyArgValTyrThrValS 1870        1880       1890       1900       1910       1920
CAAATGTTAATACCACTACAAATAACGATGGAGTTAATGATAATGGAGCTCGTTTTTCAG
erAsnValAsnThrThrThrAsnAsnAspGlyValAsnAspAsnGlyAlaArgPheSerA 1930        1940       1950       1960       1970       1980
ATATTAATATCGGTAATATAGTAGCAAGTGATAATACTAATGTAACGCTAGATATAAATG
spIleAsnIleGlyAsnIleValAlaSerAspAsnThrAsnValThrLeuAspIleAsnV 1990        2000       2010       2020       2030       2040
TGACATTAAACTCCGGTACTCCATTTGATCTCATGAATATTATGTTTGTGCCAACTAATC
alThrLeuAsnSerGlyThrProPheAspLeuMetAsnIleMetPheValProThrAsnL 2050        2060       2070       2080       2090       2100
TTCCACCACTTTATTAAGGTTTGAGTGAATGTACAATTAGTATTTTATTCTATCATAAAT
euProProLeuTyrEnd 2110        2120       2130       2140       2150       2160
TTAATAGAAAATTCTTAAACATATTGACGGAACTAAATGATATATAATTATGGATATTAG 2170        2180       2190       2200       2210       2220
AGGGTGTCTTAAAGTAGTAAAATTCTTACTCTGAGACACCCTCTTTATTTTTTTATATCC 2230        2240       2250       2260
AAATCGGATGAAATATGGGAGAAATCATTTCAAGTTAACCTAAAAGCTT
                                                HindIII
```

Figure 4A

```
         10        20        30        40        50        60
AAGCTTAATTAAAGATAATATCTTTGAATTGTAACGCCCCTCAAAAGTAAGAACTACAAA
HindIII 70        80        90       100       110       120
AAAAGAATACGTTATATAGAAATATGTTTGAACCTTCTTCAGATTACAAATATATTCGGA 130       140       150       160       170       180
CGGACTCTACCTCAAATGCTTATCTAACTATAGAATGACATACAAGCACAACCTTGAAAA 190       200       210       220       230       240
TTTGAAAATATAACTACCAATGAACTTGTTCATGTGAATTATCGCTGTATTTAATTTTCT 250       260       270       280       290       300
CAATTCAATATATAATATGCCAATACATTGTTACAAGTAGAAATTAAGACACCCTTGATA 310       320       330       340       350       360
GCCTTACTATACCTAACATGATGTAGTATTAAATGAATATGTAAATATATTTATGATAAG 370       380       390       400       410       420
AAGCGACTTATTTATAATCATTACATATTTTCTATTGGAATGATTAAGATTCCAATAGA 430       440       450       460       470       480
ATAGTGTATAAATTATTTATCTTGAAAGGAGGGATGCCTAAAAACGAAGAACATTAAAAA 490       500       510       520       530       540
CATATATTTGCACCGTCTAATGGATTTATGAAAAATCATTTTATCAGTTTGAAAATTATG 550       560       570       580       590       600
TATTATGATAAGAAAGGGAGGAAGAAAAATGAATCCGAACAATCGAAGTGAACATGATAC
           TC                     MetAsnProAsnAsnArgSerGluHisAspTh
     EcoRV
        610       620       630       640       650       660
AATAAAAACTACTGAAAATAATGAGGTGCCAACTAACCATGTTCAATATCCTTTAGCGGA
rIleLysThrThrGluAsnAsnGluValProThrAsnHisValGlnTyrProLeuAlaGl 670       680       690       700       710       720
AACTCCAAATCCAACACTAGAAGATTTAAATTATAAAGAGTTTTTAAGAATGACTGCAGA
uThrProAsnProThrLeuGluAspLeuAsnTyrLysGluPheLeuArgMetThrAlaAs 730       740       750       760       770       780
TAATAATACGGAAGCACTAGATAGCTCTACAACAAAAGATGTCATTCAAAAAGGCATTTC
pAsnAsnThrGluAlaLeuAspSerSerThrThrLysAspValIleGlnLysGlyIleSe 790       800       810       820       830       840
CGTAGTAGGTGATCTCCTAGGCGTAGTAGGTTTCCCGTTTGGTGGAGCGCTTGTTTCGTT
rValValGlyAspLeuLeuGlyValValGlyPheProPheGlyGlyAlaLeuValSerPh 850       860       870       880       890       900
TTATACAAACTTTTTAAATACTATTTGGCCAAGTGAAGACCCGTGGAAGGCTTTTATGGA
eTyrThrAsnPheLeuAsnThrIleTrpProSerGluAspProTrpLysAlaPheMetGl
```

FIGURE 4B

```
          910       920       930       940       950       960
      ACAAGTAGAAGCATTGATGGATCAGAAAATAGCTGATTATGCAAAAAATAAAGCTCTTGC
      uGlnValGluAlaLeuMetAspGlnLysIleAlaAspTyrAlaLysAsnLysAlaLeuAl 970       980       990      1000      1010      1020
      AGAGTTACAGGGCCTTCAAAATAATGTCGAAGATTATGTGAGTGCATTGAGTTCATGGCA
      aGluLeuGlnGlyLeuGlnAsnAsnValGluAspTyrValSerAlaLeuSerSerTrpGl 1030      1040      1050      1060      1070      1080
      AAAAAATCCTGTGAGTTCACGAAATCCACATAGCCAGGGGCGGATAAGAGAGCTGTTTTC
      nLysAsnProValSerSerArgAsnProHisSerGlnGlyArgIleArgGluLeuPheSe 1090      1100      1110      1120      1130      1140
      TCAAGCAGAAAGTCATTTTCGTAATTCAATGCCTTCGTTTGCAATTTCTGGATACGAGGT
      rGlnAlaGluSerHisPheArgAsnSerMetProSerPheAlaIleSerGlyTyrGluVa 1150      1160      1170      1180      1190      1200
      TCTATTTCTAACAACATATGCACAAGCTGCCAACACACATTTATTTTTACTAAAAGACGC
      lLeuPheLeuThrThrTyrAlaGlnAlaAlaAsnThrHisLeuPheLeuLeuLysAspAl 1210      1220      1230      1240      1250      1260
      TCAAATTTATGGAGAAGAATGGGGATACGAAAAGAAGATATTGCTGAATTTTATAAAAG
      aGlnIleTyrGlyGluGluTrpGlyTyrGluLysGluAspIleAlaGluPheTyrLysAr 1270      1280      1290      1300      1310      1320
      ACAACTAAAACTTACGCAAGAATATACTGACCATTGTGTCAAATGGTATAATGTTGGATT
      gGlnLeuLysLeuThrGlnGluTyrThrAspHisCysValLysTrpTyrAsnValGlyLe 1330      1340      1350      1360      1370      1380
      AGATAAATTAAGAGGTTCATCTTATGAATCTTGGGTAAACTTTAACCGTTATCGCAGAGA
      uAspLysLeuArgGlySerSerTyrGluSerTrpValAsnPheAsnArgTyrArgArgGl 1390      1400      1410      1420      1430      1440
      GATGACATTAACAGTATTAGATTTAATTGCACTATTTCCATTGTATGATGTTCGGCTATA
      uMetThrLeuThrValLeuAspLeuIleAlaLeuPheProLeuTyrAspValArgLeuTy 1450      1460      1470      1480      1490      1500
      CCCAAAAGAAGTTAAAACCGAATTAACAAGAGACGTTTTAACAGATCCAATTGTCGGAGT
      rProLysGluValLysThrGluLeuThrArgAspValLeuThrAspProIleValGlyVa 1510      1520      1530      1540      1550      1560
      CAACAACCTTAGGGGCTATGGAACAACCTTCTCTAATATAGAAAATTATATTCGAAAACC
      lAsnAsnLeuArgGlyTyrGlyThrThrPheSerAsnIleGluAsnTyrIleArgLysPr 1570      1580      1590      1600      1610      1620
      ACATCTATTTGACTATCTGCATAGAATTCAATTTCACACGCGGTTCCAACCAGGATATTA
      oHisLeuPheAspTyrLeuHisArgIleGlnPheHisThrArgPheGlnProGlyTyrTy 1630      1640      1650      1660      1670      1680
      TGGAAATGACTCTTTCAATTATTGGTCCGGTAATTATGTTTCAACTAGACCAAGCATAGG
      rGlyAsnAspSerPheAsnTyrTrpSerGlyAsnTyrValSerThrArgProSerIleGl 1690      1700      1710      1720      1730      1740
      ATCAAATGATATAATCACATCTCCATTCTATGGAAATAAATCCAGTGAACCTGTACAAAA
      ySerAsnAspIleIleThrSerProPheTyrGlyAsnLysSerSerGluProValGlnAs 1750      1760      1770      1780      1790      1800
      TTTAGAATTTAATGGAGAAAAAGTCTATAGAGCCGTAGCAAATACAAATCTTGCGGTCTG
      nLeuGluPheAsnGlyGluLysValTyrArgAlaValAlaAsnThrAsnLeuAlaValTr
```

Figure 4c

```
     1810      1820      1830      1840      1850      1860
GCCGTCCGCTGTATATTCAGGTGTTACAAAAGTGGAATTTAGCCAATATAATGATCAAAC
pProSerAlaValTyrSerGlyValThrLysValGluPheSerGlnTyrAsnAspGlnTh 1870      1880      1890      1900      1910      1920
AGATGAAGCAAGTACACAAACGTACGACTCAAAAAGAAATGTTGGCGCGGTCAGCTGGGA
rAspGluAlaSerThrGlnThrTyrAspSerLysArgAsnValGlyAlaValSerTrpAs 1930      1940      1950      1960      1970      1980
TTCTATCGATCAATTGCCTCCAGAAACAACAGATGAACCTCTAGAAAAGGGATATAGCCA
pSerIleAspGlnLeuProProGluThrThrAspGluProLeuGluLysGlyTyrSerHi 1990      2000      2010      2020      2030      2040
TCAACTCAATTATGTAATGTGCTTTTTAATGCAGGGTAGTAGAGGAACAATCCCAGTGTT
sGlnLeuAsnTyrValMetCysPheLeuMetGlnGlySerArgGlyThrIleProValLe 2050      2060      2070      2080      2090      2100
AACTTGGACACATAAAAGTGTAGACTTTTTTAACATGATTGATTCGAAAAAAATTACACA
uThrTrpThrHisLysSerValAspPhePheAsnMetIleAspSerLysLysIleThrGl 2110      2120      2130      2140      2150      2160
ACTTCCGTTAGTAAAGGCATATAAGTTACAATCTGGTGCTTCCGTTGTCGCAGGTCCTAG
nLeuProLeuValLysAlaTyrLysLeuGlnSerGlyAlaSerValValAlaGlyProAr 2170      2180      2190      2200      2210      2220
GTTTACAGGAGGAGATATCATTCAATGCACAGAAAATGGAAGTGCGGCAACTATTTACGT
gPheThrGlyGlyAspIleIleGlnCysThrGluAsnGlySerAlaAlaThrIleTyrVa 2230      2240      2250      2260      2270      2280
TACACCGGATGTGTCGTACTCTCAAAAATATCGAGCTAGAATTCATTATGCTTCTACATC
lThrProAspValSerTyrSerGlnLysTyrArgAlaArgIleHisTyrAlaSerThrSe 2290      2300      2310      2320      2330      2340
TCAGATAACATTTACACTCAGTTTAGACGGGGCACCATTTAATCAATACTATTTCGATAA
rGlnIleThrPheThrLeuSerLeuAspGlyAlaProPheAsnGlnTyrTyrPheAspLy 2350      2360      2370      2380      2390      2400
AACGATAAATAAAGGAGACACATTAACGTATAATTCATTTAATTTAGCAAGTTTCAGCAC
sThrIleAsnLysGlyAspThrLeuThrTyrAsnSerPheAsnLeuAlaSerPheSerTh 2410      2420      2430      2440      2450      2460
ACCATTCGAATTATCAGGGAATAACTTACAAATAGGCGTCACAGGATTAAGTGCTGGAGA
rProPheGluLeuSerGlyAsnAsnLeuGlnIleGlyValThrGlyLeuSerAlaGlyAs 2470      2480      2490      2500      2510      2520
TAAAGTTTATATAGACAAAATTGAATTTATTCCAGTGAATTAAATTAACTAGAAAGTAAA
pLysValTyrIleAspLysIleGluPheIleProValAsnEnd 2530      2540      2550      2560      2570      2580
GAAGTAGTGACCATCTATGATAGTAAGCAAAGGATAAAAAAATGAGTTCATAAAATGAAT 2590      2600      2610      2620      2630      2640
AACATAGTGTTCTTCAACTTTCGCTTTTTGAAGGTAGATGAAGAACACTATTTTTATTTT 2650      2660      2670      2680      2690      2700
CAAAATGAAGGAAGTTTTAAATATGTAATCATTTAAAGGGAACAATGAAAGTAGGAAATA
```

FIGURE 4D

```
       2710        2720        2730        2740        2750        2760
AGTCATTATCTATAACAAAATAACATTTTTATATAGCCAGAAATGAATTATAATATTAAT 2770        2780        2790        2800        2810        2820
CTTTTCTAAATTGACGTTTTTCTAAACGTTCTATAGCTTCAAGACGCTTAGAATCATCAA 2830        2840        2850        2860        2870        2880
TATTTGTATACAGAGCTGTTGTTTCCATCGAGTTATGTCCCATTTGATTCGCTAATAGAA 2890        2900        2910        2920        2930        2940
CAAGATCTTTATTTTCGTTATAATGATTGGTTGCATAAGTATGGCGTAATTTATGAGGGC 2950        2960        2970        2980
TTTTCTTTTCATCAAAAGCCCTCGTGTATTTCTCTGTAAGCTT
                                        HindIII
```

FIGURE 6A

```
         10        20        30        40        50        60
GAATTCTTTACTTAGGAATCCCTCACTTCTAAATGAAGTGAAAGTGGGGGTAGTTCAAAA
EcoRI 70        80        90       100       110       120
AAAGCATAGATATCTTCTTCTATAGGTGAAGATATCTATGCTTTTCTTTTTAAATTAAA 130       140       150       160       170       180
GATATACTTTACTCATACGGCAGGGAAAATTATTAACAGGAGATAATATCCAATTCTAAT 190       200       210       220       230       240
AATTGTATAAATAGTTTGAACATGTTTGAAAATTAACCAAACAATTTTTGTTTTGAAAAA 250       260       270       280       290       300
TGGATTCTCTAATACACCTGTTAATGTAACGTATGGAAAGGAGAATAGAAGCAGTTAAGA 310       320       330       340       350       360
AAGCGGTAAATGGATGATTAACTAGATTTAAGAAAGATGAAGGGTAATTTTTGAGAAATA 370       380       390       400       410       420
AAATAATCAACTGGAATGATTAGGAATTTCGGTATTGTGACAGTTTTCAAATTTTATACT 430       440       450       460       470       480
AGTAATAAATAAATTACTTTTTGAAAGTAATATCATTACAAAAGGTACTTGGAATCTTCT 490       500       510       520       530       540
TGCTTATTCCATGATTCCAAGAAAAATCGCCATTTACACACTAGTGGACCAAAATACAGA 550       560       570       580       590       600
AACAAGCGAACATGCTAGATTTGCAAATAATGGTGGTGTCTCATCTGGTATATGCTGGGT 610       620       630       640       650       660
ATTACTGTAGATGATTTAGGGAGGAGCATGATGGATGGCTAAATGTAGGCTTTCATGTTT 670       680       690       700       710       720
AAAGTATGATCCTTCCTATACCATATACAAATTATGCGTATAACAAAAGTGAGAATGATT 730       740       750       760       770       780
CCTATGTTTAAGACTTAATTAATAATTATAATCAAAGTTAGAGTTGTAATTGTGGTTGTA 790       800       810       820       830       840
AATAAGCACTTTCTTAAAAATATTCGTTATTATCAGGCTAATTTAGTATCTTTAATTTTA 850       860       870       880       890       900
ATATATTACTTAATATTTAAGGAGGAATTTTATATGAATAGTGTATTGAATAGCGGAAGA
  G  AT             RBS           MetAsnSerValLeuAsnSerGlyArg
  EcoRV
```

FIGURE 6B

```
       910       920       930       940       950       960
ACTACTATTTGTGATGCGTATAATGTAGCGGCTCATGATCCATTTAGTTTTCAACACAAA
ThrThrIleCysAspAlaTyrAsnValAlaAlaHisAspProPheSerPheGlnHisLys 970       980       990      1000      1010      1020
TCATTAGATACCGTACAAAAGGAATGGACGGAGTGGAAAAAAAATAATCATAGTTTATAC
SerLeuAspThrValGlnLysGluTrpThrGluTrpLysLysAsnAsnHisSerLeuTyr 1030      1040      1050      1060      1070      1080
CTAGATCCTATTGTTGGAACTGTGGCTAGTTTTCTGTTAAAGAAAGTGGGGAGTCTTGTT
LeuAspProIleValGlyThrValAlaSerPheLeuLeuLysLysValGlySerLeuVal 1090      1100      1110      1120      1130      1140
GGAAAAAGGATACTAAGTGAGTTACGGAATTTAATATTTCCTAGTGGTAGTACAAATCTA
GlyLysArgIleLeuSerGluLeuArgAsnLeuIlePheProSerGlySerThrAsnLeu 1150      1160      1170      1180      1190      1200
ATGCAAGATATTTTAAGAGAGACAGAAAAATTCCTGAATCAAAGACTTAATACAGACACT
MetGlnAspIleLeuArgGluThrGluLysPheLeuAsnGlnArgLeuAsnThrAspThr 1210      1220      1230      1240      1250      1260
CTTGCCCGTGTAAATGCGGAATTGACAGGGCTGCAAGCAAATGTAGAAGAGTTTAATCGA
LeuAlaArgValAsnAlaGluLeuThrGlyLeuGlnAlaAsnValGluGluPheAsnArg 1270      1280      1290      1300      1310      1320
CAAGTAGATAATTTTTTGAACCCTAACCGAAACGCTGTTCCTTTATCAATAACTTCTTCA
GlnValAspAsnPheLeuAsnProAsnArgAsnAlaValProLeuSerIleThrSerSer 1330      1340      1350      1360      1370      1380
GTTAATACAATGCAACAATTATTTCTAAATAGATTACCCCAGTTCCAGATGCAAGGATAC
ValAsnThrMetGlnGlnLeuPheLeuAsnArgLeuProGlnPheGlnMetGlnGlyTyr 1390      1400      1410      1420      1430      1440
CAACTGTTATTATTACCTTTATTTGCACAGGCAGCCAATTTACATCTTTCTTTTATTAGA
GlnLeuLeuLeuLeuProLeuPheAlaGlnAlaAlaAsnLeuHisLeuSerPheIleArg 1450      1460      1470      1480      1490      1500
GATGTTATTCTAAATGCAGATGAATGGGGAATTTCAGCAGCAACATTACGTACGTATCGA
AspValIleLeuAsnAlaAspGluTrpGlyIleSerAlaAlaThrLeuArgThrTyrArg 1510      1520      1530      1540      1550      1560
GATTACTTGAAAAATTATACAAGAGATTACTCTAACTATTGTATAAATACGTATCAAAGT
AspTyrLeuLysAsnTyrThrArgAspTyrSerAsnTyrCysIleAsnThrTyrGlnSer
```

Figure 6C

```
       1570        1580        1590        1600        1610        1620
GCGTTTAAAGGTTTAAACACTCGTTTACACGATATGTTAGAATTTAGAACATATATGTTT
AlaPheLysGlyLeuAsnThrArgLeuHisAspMetLeuGluPheArgThrTyrMetPhe 1630        1640        1650        1660        1670        1680
TTAAATGTATTTGAGTATGTATCTATCTGGTCGTTGTTTAAATATCAAAGTCTTCTAGTA
LeuAsnValPheGluTyrValSerIleTrpSerLeuPheLysTyrGlnSerLeuLeuVal 1690        1700        1710        1720        1730        1740
TCTTCCGGTGCTAATTTATATGCAAGTGGTAGTGGACCACAGCAGACCCAATCATTTACT
SerSerGlyAlaAsnLeuTyrAlaSerGlySerGlyProGlnGlnThrGlnSerPheThr 1750        1760        1770        1780        1790        1800
TCACAAGACTGGCCATTTTTATATTCTCTTTTCCAAGTTAATTCAAATTATGTGTTAAAT
SerGlnAspTrpProPheLeuTyrSerLeuPheGlnValAsnSerAsnTyrValLeuAsn 1810        1820        1830        1840        1850        1860
GGATTTAGTGGTGCTAGGCTTTCTAATACCTTCCCTAATATAGTTGGTTTACCTGGTTCT
GlyPheSerGlyAlaArgLeuSerAsnThrPheProAsnIleValGlyLeuProGlySer 1870        1880        1890        1900        1910        1920
ACTACAACTCACGCATTGCTTGCTGCAAGGGTTAATTACAGTGGAGGAATTTCGTCTGGT
ThrThrThrHisAlaLeuLeuAlaAlaArgValAsnTyrSerGlyGlyIleSerSerGly 1930        1940        1950        1960        1970        1980
GATATAGGTGCATCTCCGTTTAATCAAAATTTTAATTGTAGCACATTTCTCCCCCCATTG
AspIleGlyAlaSerProPheAsnGlnAsnPheAsnCysSerThrPheLeuProProLeu 1990        2000        2010        2020        2030        2040
TTAACGCCATTTGTTAGGAGTTGGCTAGATTCAGGTTCAGATCGGGAGGGCGTTGCCACC
LeuThrProPheValArgSerTrpLeuAspSerGlySerAspArgGluGlyValAlaThr 2050        2060        2070        2080        2090        2100
GTTACAAATTGGCAAACAGAATCCTTTGAGACAACTTTAGGGTTAAGGAGTGGTGCTTTT
ValThrAsnTrpGlnThrGluSerPheGluThrThrLeuGlyLeuArgSerGlyAlaPhe 2110        2120        2130        2140        2150        2160
ACAGCTCGCGGTAATTCAAACTATTTCCCAGATTATTTTATTCGTAATATTTCTGGAGTT
ThrAlaArgGlyAsnSerAsnTyrPheProAspTyrPheIleArgAsnIleSerGlyVal 2170        2180        2190        2200        2210        2220
CCTTTAGTTGTTAGAAATGAAGATTTAAGAAGACCGTTACACTATAATGAAATAAGAAAT
ProLeuValValArgAsnGluAspLeuArgArgProLeuHisTyrAsnGluIleArgAsn
```

Figure 6D

```
       2230      2240      2250      2260      2270      2280
ATAGCAAGTCCTTCAGGAACACCTGGTGGAGCACGAGCTTATATGGTATCTGTGCATAAC
IleAlaSerProSerGlyThrProGlyGlyAlaArgAlaTyrMetValSerValHisAsn 2290      2300      2310      2320      2330      2340
AGAAAAAATAATATCCATGCTGTTCATGAAAATGGTTCTATGATTCATTTAGCGCCAAAT
ArgLysAsnAsnIleHisAlaValHisGluAsnGlySerMetIleHisLeuAlaProAsn 2350      2360      2370      2380      2390      2400
GACTATACAGGATTTACTATTTCGCCGATACATGCAACTCAAGTGAATAATCAAACACGA
AspTyrThrGlyPheThrIleSerProIleHisAlaThrGlnValAsnAsnGlnThrArg 2410      2420      2430      2440      2450      2460
ACATTTATTTCTGAAAAATTTGGAAATCAAGGTGATTCTTTAAGGTTTGAACAAAACAAC
ThrPheIleSerGluLysPheGlyAsnGlnGlyAspSerLeuArgPheGluGlnAsnAsn 2470      2480      2490      2500      2510      2520
ACGACAGCTCGTTATACGCTTAGAGGGAATGGAAATAGTTACAATCTTTATTTAAGAGTT
ThrThrAlaArgTyrThrLeuArgGlyAsnGlyAsnSerTyrAsnLeuTyrLeuArgVal 2530      2540      2550      2560      2570      2580
TCTTCAATAGGAAATTCCACTATTCGAGTTACTATAAACGGTAGGGTATATACTGCTACA
SerSerIleGlyAsnSerThrIleArgValThrIleAsnGlyArgValTyrThrAlaThr 2590      2600      2610      2620      2630      2640
AATGTTAATACTACTACAAATAACGATGGAGTTAATGATAATGGAGCTCGTTTTTCAGAT
AsnValAsnThrThrThrAsnAsnAspGlyValAsnAspAsnGlyAlaArgPheSerAsp 2650      2660      2670      2680      2690      2700
ATTAATATCGGTAATGTAGTAGCAAGTAGTAATTCTGATGTACCATTAGATATAAATGTA
IleAsnIleGlyAsnValValAlaSerSerAsnSerAspValProLeuAspIleAsnVal 2710      2720      2730      2740      2750      2760
ACATTAAACTCCGGTACTCAATTTGATCTTATGAATATTATGCTTGTACCAACTAATATT
ThrLeuAsnSerGlyThrGlnPheAspLeuMetAsnIleMetLeuValProThrAsnIle 2770      2780      2790      2800      2810      2820
TCACCACTTTATTAAAGTTTGAGGTTCTTATGTAAATATAAGTTTATAGTTTTGATCTA
SerProLeuTyrEnd 2830      2840      2850      2860      2870      2880
TCTACTAAAATTAAGTATATATAATGTATGGATGTTAGAGGTTGTCTTAAAGTAGTTGAA 2890      2900      2910      2920
TGATTACTCTGAGGCAACCTCTTTATTTTTATTCTTAGGAATTC
                                     ‾‾‾‾‾‾
                                      EcoRI
```

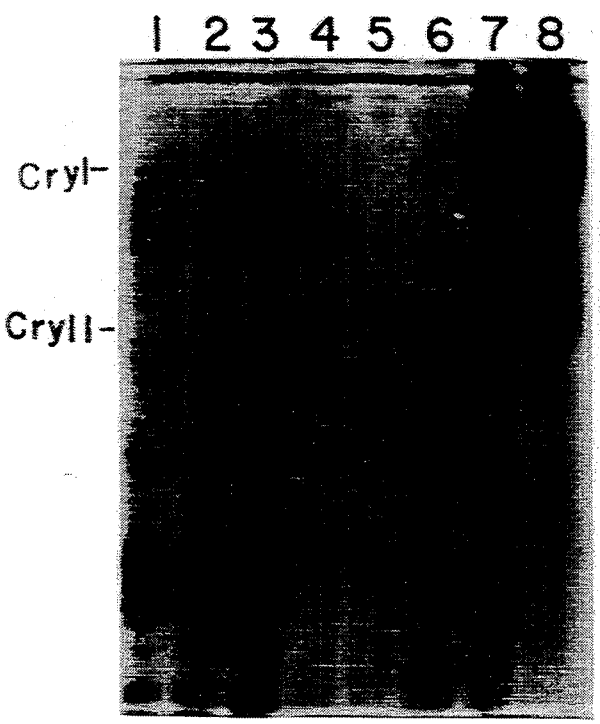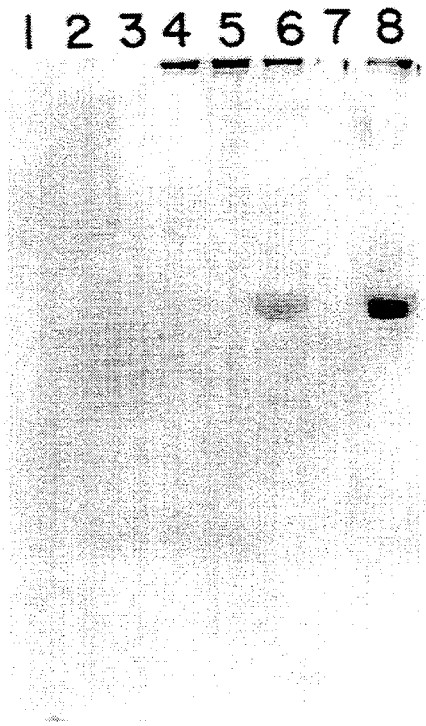
FIGURE 7
FIGURE 8

CRYIIB PROTEIN, INSECTICIDAL COMPOSITIONS AND METHODS OF USE THEREOF

CROSS-REFERENCE TO RELATED APPLICATION

This application is a continuation of U.S. patent application Ser. No. 07/751,452, filed Aug. 28, 1991, now abandoned which is a division of U.S. patent application Ser. No. 07/379,015, filed Jul. 11, 1989, now U.S. Pat. No. 5,073,632, which was a continuation-in-part of U.S. patent application Ser. No. 07/039,542, filed Apr. 16, 1987, now abandoned.

FIELD OF THE INVENTION

The present invention relates to a gene isolated from *Bacillus thuringiensis* (hereinafter "B.t.") encoding an insecticidal crystal protein CryIIB, as well as insecticidal compositions containing the protein. The insecticidal compositions are toxic to insects of the order Lepidoptera. To enhance the production of the protein, the promoter region of a cryIIIA crystal protein gene is transcriptionally fused to the cryIIB gene.

BACKGROUND OF THE INVENTION

B.t. is a gram-positive soil bacterium which produces crystal proteins during sporulation which are specifically toxic to certain orders and species of insects. Many different strains of B.t. have been shown to produce insecticidal crystal proteins. Compositions including B.t. strains which produce insecticidal proteins have been commercially available and used as environmentally acceptable insecticides because they are quite toxic to the specific target insect, but are harmless to plants and other non-targeted organisms.

A number of genes encoding crystal proteins have been cloned from several strains of B.t. A good overview is set forth in H. Höfte et al., *Microbiol. Rev.*, 53, pp. 242-255 (1989). While this reference is not prior art with respect to the present invention, it provides a good overview of the genes and proteins obtained from B.t. and their uses, a nomenclature and classification scheme, and has an extensive bibliography.

Also see A. R. Aronson, et al., *Microbiol. Rev.*, 50, pp. 1-24 (1986) for an earlier review of work relating to the insecticidal activity of B.t..

The B.t. crystal protein is active in the insect only after ingestion. After ingestion by a lepidopteran insect, the alkaline pH and proteolytic enzymes in the mid-gut solubilize the crystal allowing the release of the toxic components. These toxic components poison the mid-gut cells causing the insect to cease feeding and, eventually, to die. In fact, B.t. has proven to be an effective and environmentally safe insecticide in dealing with lepidopteran pests.

One predominant class of toxin crystal proteins produced by many of the B.t. strains is known as the P-1 type of proteins (and more recently as the CryI type of proteins). The CryI proteins have molecular masses of about 130,000 Daltons (Da). The genes for the CryI crystal proteins as well as those of other crystal protein genes have been discovered to reside on large plasmids that occur naturally in B.t.

The present invention is a result of developments by the inventor, building on his experience with other B.t. genes and proteins. The inventor has isolated and purified a gene identified as cryIIA (previously referred to as the "P-2," "cryB1" or the "cryBI" gene) and the encoded CryIIA protein (previously referred to variously as the "P2 protein," "P-2 toxin," "P-2 delta-endotoxin" or "CryB1" protein) resulting from the cryIIA gene expression. These are disclosed and claimed in the Parent Application. The cryIIA gene, obtained from *B.t.* var. *kurstaki* (hereinafter "B.t.k.") strain HD-263 is also described in W. P. Donovan et al., *J. Biol. Chem.*, 263, PP. 561-567 (1988) (hereinafter "Donovan (1)"), with a correction to the nucleotide sequence of the cryIIA gene and the amino acid sequence of the CryIIA protein published in W. P. Donovan, et al., *J. Biol. Chem.*, 264, p. 4740 (1989) (hereinafter "Donovan (2)"). The CryIIA gene contains 633 codons and encodes a CryIIA protein having a molecular mass of 70,860 Da. As reported in Donovan (1) and in T. Yamamoto et al., *Biochem. Biophys. Res. Commun.*, 103, pp. 414-421 (1981), the CryIIA protein is toxic to both lepidopteran (caterpillars) and dipteran (mosquitos) insects.

In connection with the work relating to the cryIIA gene and CryIIA protein, the inventor discovered that B.t.k. contains a nucleotide sequence related to the cryIIA gene which was designated cryIIB (previously referred to as the "cryBI-related" sequence or "cryBII" sequence). The cryIIB gene has 633 codons and encodes a protein of 70,749 Da, the CryIIB protein (previously referred to as "CryB2"). Using the nucleotide sequence comparison program of C. Queen et al., *Nucleic Acids Res.*, 12, pp. 581-599 (1984), it was determined that the protein coding region of 1,899 nucleotides of the cryIIB gene contained 89% positional identity with the protein coding region of 1,899 nucleotides of the cryIIA gene. Additionally, 557 out of 633 of the amino acids in the CryIIB protein were positionally identical to the corresponding amino acids in the CryIIA protein (88%). While the CryIIA and CryIIB proteins appear to be similar, measurement of their insecticidal activities indicated a substantially different insect toxicity between the two proteins. Thus, the proteins are related, but they clearly differ in their amino acid sequences and in their insecticidal activities.

The cryIIB gene and CryIIB protein were also investigated independently by other researchers as reported in W. R. Widner et al., *J. Bacteriol*, 171, pp. 965-974 (1989), published less than one year before the filing of the present application. Widner et al. (1989) reported a nucleotide sequence for the cryIIA gene (referred to in the article as a "cryB1" gene) and a cryIIB gene (referred to in the article as a "cryB2" gene). The nucleotide sequence for the cryB2 gene reported in Widner et al. (1989) is identical to the protein coding region of the cryIIB gene of the present invention with the exception of a translationally silent difference at nucleotide 1035 which the present inventor has found to be thymine, but which Widner et al. (1989) report as cytosine.

As explained hereinafter, the inventor also determined that the cryIIB gene did not express well with its native promoter, such that the CryIIB protein was produced in minimal amounts, if at all, in the native B.t. strains. Accordingly, as part of the present invention, the inventor created a recombinant hybrid fusion gene in which the promoter from the cryIIIA gene was fused to the protein coding region of the cryIIB gene. This resulted in substantially enhanced production of the CryIIB protein.

The cryIIIA gene and its product, the CryIIIA protein (referred to previously as the "cryC" gene and "CryC" protein) are described in W. P. Donovan et al., *Mol. Gen. Genet.*, 214, pp. 365–372 (1988) (hereinafter "Donovan (3)"). The cryIIIA gene was isolated from a new strain of B.t. (designated EG2158) toxic to larva of *Lepinotarsa decemlineata* (Colorado potato beetle). The cryIIIA gene isolated by the inventor apparently is identical to a gene of *B.t.* var. *tenebrionis*, as reported by V. Sekar, et al., *Proc. Natl. Acad. Sci. USA*, 84, pp.7036–7040 (1987), and by H. Höfte, et al., *Nucleic Acids Res.*, 15, p. 7183 (1987), as well as to a gene isolated from *B.t.* var. *san diego*, reported by C. Herrnstadt, et al., *Gene*, 57, pp. 37–46 (1987). B.t. strain EG2158 differs in several ways from *B.t. tenebrionis* and *B.t. san diego*.

SUMMARY OF THE INVENTION

One aspect of the present invention relates to a purified and isolated gene having a nucleotide sequence coding for the amino acid sequence illustrated in FIG. 6 extending from nucleotides 874 through 2775, the insecticidal protein produced by such gene and an insecticidal composition comprising the protein and a carrier.

Another aspect of the present invention relates to a recombinant hybrid gene comprising DNA obtained from two separate nucleotide sequences, one nucleotide sequence being a coding nucleotide sequence for a CryIIB protein, and the other nucleotide sequence being a promoter nucleotide sequence, the coding nucleotide sequence for the CryIIB protein coding for the amino acid sequence illustrated in FIG. 6 extending from nucleotides 874 through 2775, the promoter nucleotide sequence being a foreign promoter nucleotide sequence having an ability to promote the production of more of the CryIIB protein than the promoter nucleotide sequence naturally occurring with respect to the coding nucleotide sequence. The promoter nucleotide sequence is the nucleotide sequence illustrated in FIG. 4 from nucleotides 1 through 549, and its equivalents.

BRIEF DESCRIPTION OF THE DRAWINGS

FIGS. 2A through 2C cryIIA gene and the amino acid sequence of the CryIIA (P-2) protein deduced from the DNA nucleotide sequence.

FIG. 4 comprises FIGS. 4-1 through 4-4 and shows the DNA nucleotide sequence of the cryIIIA gene, with its promoter region and coding region, and the amino acid sequence of the CryIIIA (CryC) protein deduced from the DNA nucleotide sequence.

Figure 1:
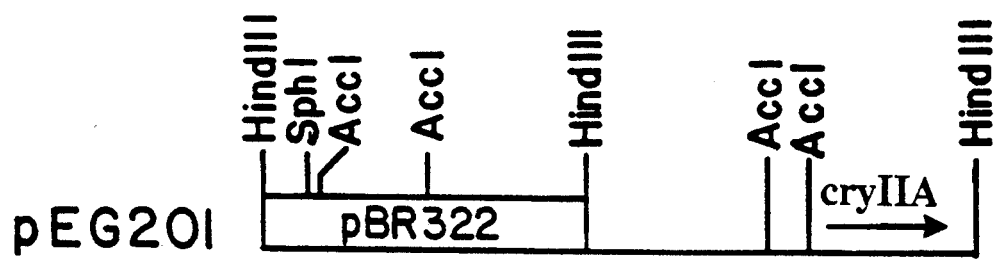
FIG. 1 is a restriction map of the recombinant plasmid pEG201 that contains the cloned cryIIA (cryBI or P-2) gene. The location and direction of transcription of the cryIIA gene are indicated by the arrow.

pEG230 comprises a 9.0 kilobase (kb) HindIII cryIIB fragment from B.t. strain HD1 cloned into the HindIII site of plasmid pBR322.

pEG243 comprises the plasmid pEG230 into which is inserted the Bacillus vector pNN101 at the SphI site of pEG230.

pEG254 comprises the vector M13mp18 into which is inserted the 2.9 kb EcoRI cryIIB fragment from pEG230. Site-directed mutagenesis was used to create an EcoRV site upstream from cryIIB at nucleotide 847.

pEG256 comprises a vector M13mp18 into which is inserted the 3.0 kb HindIII cryIIIA fragment from B.t. strain EG2158. Site-directed mutagenesis was used to create an EcoRV site upstream from the cryIIIA gene at nucleotide 549.

pEG255 comprises a vector made by subcloning the 2.1 kb EcoRV-EcoRI fragment containing the cryIIB protein coding region from pEG254 into the 7.8 kb EcoRV-EcoRI fragment containing the 0.5 kb cryIIIA promoter region from pEG256 plus M13mp18.

pEG245 comprises the Bacillus-*E. coli* shuttle vector pEG147 into which is inserted the 2.6 kb HindIII-EcoRI fragment containing the cryIIIA/cryIIB fusion gene from pEG255 at the HindIII-EcoRI sites of the shuttle vector pEG147.

FIGS. 6A through 6D cryIIB gene and the amino acid sequence of the CryIIB protein deduced from the DNA nucleotide sequence.

FIG. 7A is a photograph of a Coomassie stained sodium dodecyl sulfate (SDS)-polyacrylamide gel in which each of lanes 1 through 8 shows proteins extracted from 600 μg (wet weight) of the following strain cultures, which are characterized more fully in Table 2: lane 1, *E. coli* EG1339; lane 2, *E. coli* EG1344; lane 3, *E. coli* EG7208; lane 4, B.t. EG7211; lane 5, B.t. EG7203; lane 6, B.t. EG7210; lane 7, B.t. HD-122; lane 8, B.t. HD-1. CryI indicates the position of the CryI-type of proteins. CryII indicates the position of the CryIIA and CryIIB proteins.

FIG. 7B illustrates a nitrocellulose filter onto which the proteins from FIG. 7A were blotted, where the filter was probed with anti-CryIIA antibodies.

DESCRIPTION OF THE PREFERRED EMBODIMENTS

As indicated above, the present invention relates to an isolated and purified cryIIB gene and the CryIIB protein encoded by the gene. Since the native promoter region for the cryIIB gene does not provide for abundant expression of the gene, a recombinant gene was constructed in which the native promoter for the cryIIB gene was replaced by the promoter region of another crystal protein gene, the cryIIIA gene. This recombinant gene, referred to hereinafter as the "cryIIIA/IIB fusion gene" results in abundant production of the CryIIB protein.

Three genes are involved in the development of the present invention, the cryIIA gene, which was used as a probe to identify and isolate the cryIIB gene, the cryIIB gene itself, and the cryIIIA gene, the promoter portion of which is fused with the protein coding region of the cryIIB gene. Since all three genes are involved, the isolation and sequencing of all three genes are described herein, even though the isolation and sequencing of the cryIIA gene is set forth in the parent application.

In general, the techniques involved in isolating and sequencing of the three genes, in subcloning portions of the genes into various vectors and in forming the cryIIIA/IIB fusion gene are themselves well known to those skilled in the art. The isolated cryIIB gene and the cryIIIA/IIB fusion gene are novel, however. The techniques will be described both generally and specifically with respect to the genes involved herein.

To assure the availability of materials to those interested members of the public upon the issuance of a patent on the present application, deposits of the following microorganisms were made prior to the filing of the present application with the ARS Patent Collection, Agricultural Research Culture Collection, Northern Regional Research Laboratory (NRRL), Peoria, Ill. 61604 as indicated in the following Table 1:

TABLE 1

| Bacterial Strain | | Plasmids | Accession No. |
| --- | --- | --- | --- |
| B.t.k. | HD-1 | Several naturally occurring. | B-18201 |
| B.t.k. | HD263-1 | Several naturally occurring. | B-18202 |
| E. coli | EG1304 | pEG201 | B-18204 |
| B.t. morrisoni | EG2158 | Several naturally occurring | B-18213 |
| B.t.k. | HD73-26 | (plasmid recipient) | B-18508 |
| B.t. | EG7203 | pEG243 | B-18518 |
| B.t. | EG7210 | pEG245 | B-18519 |

B.t. strains HD-1, HD-263 and HD-73 (progenitor of strain HD73-26, which in turn is the background of strains EG7203 and EG7210) are available from USDA, ARS, Cotton Insects Research Unit, P.O. Box. 1033, Brownsville, Tex. 78520.

The cryIIA, cryIIIA and cryIIB genes were all isolated and sequenced using the following general techniques.

The B.t. strains harboring the cryIIA, cryIIIA and cryIIB genes (described more fully hereinafter) were cultured using standard media and fermentation techniques. Upon completion of the fermentation cycle, the bacteria were harvested by first separating the B.t. spores and crystals from the fermentation broth by centrifugation. Crystal proteins were purified by solubilizing the proteins in a buffer solution and fractionating the solubilized proteins by sodium dodecyl sulfate polyacrylamide gel electrophoresis (SDS-PAGE). After the SDS-PAGE fractionation, a gel slice containing the desired protein was excised and the protein was purified from the gel slice by electroelution.

The $NH_2$-terminal amino acid sequence of the protein under consideration was determined by automated Edman degradation using commercially available equipment. Based on the $NH_2$-terminal amino acid sequence of the protein, an oligonucleotide was designed to be used to isolate the gene for the protein. For the isolation of the cryIIA and the cryIIIA genes, radioactively labeled oligonucleotide probes were used which specifically bound or hybridized to the $NH_2$-terminal protein coding region of the gene. Again, the oligonucleotide probe technique is well known to those skilled in the art.

For the cryIIB gene, the cryIIA nucleotide sequence was radioactively labeled and used as a probe for cryII-type genes.

Plasmid libraries were obtained by digesting the total DNA isolated from bacteria containing the gene of interest with various restriction enzymes, such as HindIII, EcoRI, EcoRV, AccI, and the like. Size-selected DNA fragments were obtained by electrophoresing the digested DNA through an agarose gel, excising gel slices and separating DNA fragments from the gel slices by electroelution. The plasmid library was then constructed by ligating the size-selected DNA fragments into various plasmid vectors, such as the E. coli vector pBR322, which is readily available. Other well-known and available plasmids or vectors could be used in appropriate circumstances if desired.

The plasmid library was then transformed into cells of a host organism such as E. coli that does not contain the gene of interest. The host cells were spread on a selective solid medium, usually one containing an antibiotic, that allows only transformed cells containing recombinant plasmids to grow into colonies. Individual transformed host colonies were tested for the acquisition of the gene from the donor organism. In host colonies, the acquired gene is carried on the recombinant plasmid. The oligonucleotide probe (or the cryIIA gene, itself used as a probe for the cryIIB gene) was added under hybridization conditions that permit the probe to bind specifically to a transformed host colony containing the gene of interest. Once such a colony was identified by the probe, the recombinant plasmid contained in the colony was isolated. This recombinant plasmid contains the gene of interest. Thereafter, the nucleotide sequence of the gene was determined by the standard Sanger dideoxy method. From the nucleotide sequence, the amino acid sequence of the protein was deduced.

The CryIIB protein is a potent insecticidal compound with activity against lepidopteran insects. It is, therefore, within the scope of the invention that the CryIIB protein toxin be utilized as an insecticide (the active ingredient). The insecticidal CryIIB crystal protein may be used in homogeneous or pure form or may be included within or in association with a transformed microorganism which expresses a cloned cryIIB gene or cryIIIA/IIB fusion gene and, optionally, other toxin genes also present in the transformed microorganism. The compositions of the invention containing the CryIIB protein are applied at an insecticidally effective amount which will vary depending on such factors as, for example, the specific lepidopteran insects to be controlled, the specific plant to be treated and the method of applying the insecticidally active compositions.

The preferred insecticide formulations are made by mixing the CryIIB protein alone or incorporated in or associated with a transformed microorganism, with the desired carrier. The formulations may be administered as a dust or as a suspension in oil (vegetable or mineral) or water, a wettable powder or in any other material suitable for agricultural application, typically by spraying, using the appropriate carrier adjuvants. Suitable carriers can be solid or liquid and correspond to the substances ordinarily employed in formulation technology, e.g., dispersants, wetting agents, tackifiers, binders or fertilizers.

The formulations containing a solid or liquid adjuvant are prepared in known manner, e.g., by homogeneously mixing and/or grinding the active ingredients with extenders, e.g., solvents, solid carriers, and in some cases surface active compounds (surfactants).

Suitable liquid carriers are vegetable oils, such as coconut oil or soybean oil, mineral oils or water. The solid carriers used, e.g., for dusts and dispersible powders, are normally natural mineral fibers such as calcite, talcum, kaolin, or attapulgite. In order to improve the physical properties, it is also possible to add highly dispersed silicic acid or highly dispersed absorbent polymers. Suitable granulated absorbent carriers are porous types, for example pumice, broken brick, sepiolite or bentonite. Suitable nonsorbent carriers are materials such as silicate or sand. In addition, a great number of pregranulated materials or inorganic or organic mixtures can be used, e.g., especially dolomite or pulverized plant residues.

Depending on the nature of the active ingredients to be formulated, suitable surface-active compounds are non-ionic, cationic and/or anionic surfactants having good emulsifying, dispersing and wetting properties. The term "surfactants" will also be understood as comprising mixtures of surfactants.

These are only examples and the proteins of the present invention may be carried on any of the other well-known inert carriers.

A preferred carrier includes the microorganism host. The recombinant cryIIIA/IIB fusion gene or its equivalent, hereinafter sometimes referred to as the "toxin gene" can be introduced into a wide variety of microorganism hosts. Expression of the gene results in the production of insecticidal CryIIB crystal protein toxin. With suitable hosts, such as B.t. or other species of Bacillus, such as *B. subtilis* or *B. megaterium*, for example, the microorganism with the CryIIB crystal toxin can be applied to the situs of caterpillars of the order Lepidoptera where they will be ingested by the susceptible insects. Ingestion of a lethal amount and, in some cases, a sublethal amount, of the crystal toxin results in controlling the insects.

Alternatively, the microorganism hosting the toxin gene can be treated under conditions that prolong the activity of the toxin produced by the cell. The treated cell then can be applied to the environment of the target pests. The resulting product retains the toxicity of the CryIIB protein toxin.

Various procedures well known to those skilled in the art are available for introducing the gene expressing the toxin into the microorganism host under conditions which allow for stable maintenance and expression of the gene.

The transformants can be isolated in accordance with conventional ways, usually employing a selection technique, which allows for selection of the desired organism as against unmodified organisms or transferring organisms, when present. The transformants then can be tested for pesticidal activity. Again, these techniques are standard procedures.

Characteristics of particular interest in selecting a host cell for purposes of production include ease of introducing the gene into the host, availability of expression systems, efficiency of expression, stability of the pesticide in the host, and the presence of auxiliary genetic capabilities. The cellular host containing the pesticidal gene may be grown in any convenient nutrient medium, where the DNA construct provides a selective advantage, typically to sporulation. The sporulated cells may then be harvested in accordance with conventional ways.

The pesticidal concentration will vary widely depending upon the nature of the particular formulation, particularly whether it is a concentrate or to be used directly. The pesticide will be present in a least 1% by weight and may be 100% by weight. The dry formulations will have from about 1 to about 95% by weight of the pesticide while the liquid formulations will generally be from about 1 to about 60% by weight of the solids in the liquid phase. These formulations will be administered at about 50 mg (liquid or dry) to 1 kg or more per hectare.

The formulations can be applied to the environment of the pest(s), e.g., plants, soil or water, by spraying, dusting, sprinkling, soaking, soil injection, seed coating, seedling coating or spraying, or the like.

The carrier or host for the insecticidal composition including the CryIIB protein of the present invention may be a plant into which a gene capable of producing the CryIIB protein is inserted.

Genetic engineering of plants may be accomplished by introducing the desired DNA containing the gene into plant tissues or cells using DNA molecules of a variety of forms and origins. These include, but are not limited to DNA molecules derived from naturally occurring plant vectors such as the Ti plasmid from *Agrobacterium tumefaciens* or plant pathogens such as DNA viruses like Cauliflower Mosaic virus (CaMV) or Geminiviruses, RNA viruses, and viroids; DNA molecules derived from unstable plant genome components like extrachromosomal DNA elements in organelles (e.g., chloroplasts or mitochondria), or nuclearly encoded controlling elements; DNA molecules from stable plant genome components (e.g., origins of replication and other DNA sequences which allow introduced DNA to integrate into the organellar or nuclear genomes and to replicate normally, to autonomously replicate, to segregate normally during cell division and sexual reproduction of the plant and to be inherited in succeeding generations of plants).

DNA containing the cryIIB gene, the cryIIIA/IIB fusion gene or any other gene capable of producing the CryIIB protein may be delivered into the plant cells or tissues directly by infectious plasmids, such as Ti, viruses or microorganisms like *A. tumefaciens*, the use of liposomes, microinjection by mechanical methods and by whole chromosomes or chromosome fragments.

Although the hybrid fused cryIIIA/IIB gene as described and claimed herein has a particular promoter region and a particular encoding region for the CryIIB protein toxin, slight variations may be made in the nucleotide sequences, since the various amino acids forming the protein encoded by the gene usually may be determined by more than one codon as is well known to those skilled in the art. Moreover, there may be some variations in the nucleotide sequence which promotes the production of the CryIIB protein which will still result in a more abundant production of the protein toxin than the native promoter on the CryIIB gene. These variations which can be determined without undue experimentation by those of ordinary skill in the art with reference to the present specification are to be considered within the scope of the appended claims, since they are fully equivalent to the specifically claimed subject matter. Accordingly, the present invention also encompasses any DNA molecule including a nucleotide sequence encoding the amino acid sequence forming the CryIIB protein toxin.

The present invention will now be described in more detail with reference to the following specific, non-limiting examples. The examples relate to work which was actually done based on techniques generally known in the art and using commercially available equipment. All percentages are by weight and all solvent mixture proportions are by volume, unless otherwise noted.

Examples 1 through 3 relate to the isolation and expression of the cryIIA gene.

EXAMPLE 1

Culturing B.t.k. Strain HD1, Purification of CryIIA Protein, Determination of NH$_2$-Terminal Sequence of the CryIIA Protein and Preparation of Oligonucleotide Probe Cells of B.t.k. strain HDI-1, a single colony isolate immediately derived from parent strain HD-1 (USDA, Cotton Insect Research Unit, Brownsville, Tex. 78520), were grown in C2 medium (1% glucose, 0.2% peptone, 0.5% NZ Amine-A, casein hydrozylate (Sheffield Products), 0.2% yeast extract, 15 mM (NH$_4$)$_2$SO$_4$, 23 mM KH$_2$PO$_4$, 27 mM K$_2$HPO$_4$, 1 mM MgSO$_4$.7H$_2$O, 600 $\mu$M CaCl$_2$, 17 $\mu$M ZnSO$_4$.7H$_2$O, 17 $\mu$M CuSO$_4$.5H$_2$O, 2 $\mu$M FeSO$_4$.7H$_2$O) at 30° C. for 72 hours and spores plus crystals were harvested by centrifugation. The spore/crystal pellet was washed with several changes of 1M NaCl and then several changes of deionized water. Toxin proteins were solubilized by incubating the spore/crystal preparation in 5% B-mercaptoethanol, 2% SDS, 60 mM Tris pH 6.8, 10% glycerol at 70° C. for 7 min., and spores were removed by centrifugation.

The supernatant was subjected to electrophoresis through an SDS-polyacrylamide gel to separate proteins. The SDS-polyacrylamide gel was stained with Coomassie dye and gel slices containing the CryIIA (P-2) protein were cut out with a razor blade. The homogeneous CryIIA protein preparation was electroeluted from gel slices and, after acetone precipitation, the NH$_2$-terminal amino acid sequence of the CryIIA protein was determined by automated Edman degradation carried out on an Applied Biosystems Gas Phase Sequenator (Model 470A) and analyzed on a DuPont Zorbax C$_{18}$ column in a Hewlett-Packard HPLC (Model 1090) with a 1040 diode array detector. The amino acid sequence of the NH$_2$-terminal portion of the homogeneous CryIIA protein was determined to be:

| 1   | 2   | 3   | 4   | 5   | 6   | 7   | 8   | 9   | 10  | 11  | 12  | 13  |
|-----|-----|-----|-----|-----|-----|-----|-----|-----|-----|-----|-----|-----|
| MET | ASN | ASN | VAL | LEU | ASN | SER | GLY | ARG | THR | THR | ILE | ASN |
| 14  | 15  | 16  | 17  | 18  | 19  | 20  | 21  | 22  | 23  | 24  | 25  | 26  |
| ASP | ALA | TYR | ASN | VAL | VAL | ALA | HIS | ASP | PRO | PHE | SER | GLY |

A 62 mer oligonucleotide probe encoding amino acids 4 through 24 of the NH$_2$-terminus of the CryIIA protein was synthesized on an Applied Biosystems DNA synthesizer (Model 380A). The oligonucleotide probe was designed to bind only to the NH$_2$-terminal coding region of the cryIIA gene. The sequence of the cryIIA gene-specific oligonucleotide probe was:

5'-GTA TTA AAT TCA GGA AGA ACA ACA ATT AAT GAT GCA TAT AAT GTA GTA GCA CAT GAT CCA TT-3'.

EXAMPLE 2

Cloning of cryIIA Gene to Determine Nucleotide Sequence of cryIIA Gene and Amino Acid Sequence of CryIIA Protein The oligonucleotide probe was used to determine the size of a restriction fragment of B.t. DNA that contained at least the NH$_2$-terminal coding region of the cryIIA gene. For this determination, strain HD263-1, a single colony isolate immediately derived from parent strain HD-263 (USDA, Cotton Insect Research Unit, Brownsville, Tex. 68520), and strain HD1-1 were used as a source of DNA. Both of these strains were known to produce the CryIIA crystal protein. B.t. strains EG2158 and HD-567 which do not produce CryIIA crystal protein were used as negative controls.

DNA was isolated from the various donor strains after growth of the cells to mid-log phase at 30° C. in LB medium. Cells were harvested by centrifugation, resuspended in 50 mM Tris HCl pH 7.8, 10 mM EDTA, 1 mg/ml lysozyme and incubated at 37° C. for 60 min. Cells were lysed by adding SDS to a final concentration of 0.2%. Cell lysates were extracted twice with an equal volume of phenol and once with an equal volume of chloroform/isoamyl alcohol (24/1). One tenth volume of 3M NaAcetate and 2 volumes of EtOH were added to the lysates and DNA was extracted by spooling on a glass rod. The spooled DNA was soaked in 66% EtOH for 5 min. and in diethyl ether for 1 min. The spooled DNA was air dried and resuspended in deionized water.

Hybridization experiments were performed by digesting total DNA from each of the donor strains with HindIII restriction enzyme, electrophoresing the digested DNA on an agarose gel and transferring the DNA from the agarose gel to a nitrocellulose filter by the blot technique of Southern (J. Molec. Biol., 98 pp. 508–517 (1978)). The nitrocellulose filter was incubated at 32° C. for 16 hours in a solution of 3×SSC (1×SSC=0.15M NaCl/0.015M sodium citrate), 0.1% SDS, 220 $\mu$g/ml heparin, 10×Denhardt's (1×=0.02% bovine serum albumin/0.02% Ficoll/0.02% polyvinylpyrrolidone), containing approximately 1 $\mu$g of the cryIIA gene-specific oligonucleotide probe that had been radioactively labelled with gamma-P$^{32}$-ATP and using T4 kinase. After hybridization the nitrocellulose filter was washed with 3×SSC, 0.1% SDS at 32° C. for one hour and the filter was exposed to X-ray film. The resulting autoradiogram showed that the oligonucleotide probe specifically hybridized to two HindIII fragments of DNA, from strains HD263-1 and HD1-1, of approximately 9.0 kb and 5.0 kb. The probe failed to hybridize to any DNA restriction fragments from two strains of B.t. that did not synthesize CryIIA crystal protein, EG2158 and HD-567.

It was necessary to determine which of the two HindIII fragments, 9.0 or 5.0 kb, hybridized most strongly to the oligonucleotide probe since the most strongly hybridizing fragment would be most likely to contain the cryIIA gene. Strength of hybridization is measured by the highest temperature at which the probe remains bound to the DNA fragment on the nitrocellulose filter. Accordingly, the nitrocellulose filter was repeatedly washed in 3×SSC, 0.1% SDS at progressively higher temperatures, each wash being followed by autoradiography, until a temperature was reached (50° C.) at which the radioactive probe no longer hybridized to the 9.0 kb fragment but was seen to hybridize exclusively to the 5.0 kb fragment. Therefore, it was determined that at least the NH$_2$-terminal coding region of the cryIIA gene resided on the 5.0 kb HindIII fragment of DNA from strains HD263-1 and HD1-1.

A cryIIA gene-enriched plasmid library was constructed by digesting HD263-1 total DNA with HindIII, electrophoresing the digested DNA on an agarose gel and excising gel slices containing HindIII DNA fragments ranging in size from approximately 4.0 to 6.0 kb. HD263-1 HindIII fragments ranging in size from 4.0 to 6.0 kb were electroeluted from agarose gel slices, phenol plus chloroform extracted, ethanol precipitated and ligated into the HindIII site of plasmid pBR322 that had been digested with HindIII and treated with alkaline phosphatase. Alkaline phosphatase greatly increased the probability that recombinant plasmids were formed consisting of pBR322 plus a HindIII fragment of HD263-1 DNA. The resulting ligation mix consisted of a library of recombinant plasmids enriched for the cryIIA toxin gene from strain HD263-1.

The cryIIA gene-enriched plasmid library was transformed into an ampicillin sensitive host strain of *E. coli*, HB101 (Bethesda Research Laboratories, Bethesda, Md.), by the $CaCl_2$ procedure. *E. coli* strain HB101 does not synthesize CryIIA protein and, therefore, it would not be expected to contain the cryIIA gene. *E. coli* was used as the host strain because these cells are easily transformed with recombinant plasmids. Since pBR322 confers resistance to ampicillin, all host cells acquiring a recombinant plasmid would become ampicillin resistant. After exposure to the recombinant plasmids, the *E. coli* host cells were spread onto solid medium containing ampicillin and those cells that harbored a recombinant plasmid were able to grow into colonies. It was expected that each individual ampicillin resistant host colony would harbor many identical copies of a recombinant plasmid comprised of pBR322 plus a unique HindIII fragment from the donor strain HD263-1 DNA. However, the unique HD263-1 HindIII fragment in the recombinant plasmid would differ from one colony to the next.

Approximately two thousand individual ampicillin resistant colonies were blotted onto nitrocellulose filters. The recombinant plasmids contained in the colonies were bound to the nitrocellulose filters by treating the colonies with NaOH and $NH_4$ acetate. The resulting nitrocellulose filters contained an array of recombinant plasmids each of which was physically separated from other recombinant plasmids. The nitrocellulose filters were hybridized at 50° C. for 16 hours in a solution of 3×SSC, 200μg/ml heparin, 0.1% SDS, 10×Denhardt's and approximately 1 μg of the cryIIA gene-specific oligonucleotide probe that had been radioactively labelled. The filters were washed at 50° C. for one hour in 3×SSC, 0.1% SDS and were exposed to X-ray film. The resulting autoradiogram showed that the oligonucleotide probe had hybridized to recombinant plasmids at four different locations on the nitrocellulose filters.

By aligning the autoradiogram with the colony replicas, it was possible to identify four colonies whose recombinant plasmids had apparently hybridized with the oligonucleotide probe.

The recombinant plasmids were extracted from each of the four colonies. The plasmids were digested with HindIII and electrophoresed on an agarose gel. Three of the four plasmids consisted of pBR322 plus an apparently identical sized 5.2 kb HindIII fragment of HD263-1 DNA. The plasmids were transferred from the agarose gel to a nitrocellulose filter by the blot procedure of Southern. The nitrocellulose filter was hybridized with the radioactively labelled oligonucleotide probe and exposed to X-ray film. The resulting autoradiogram showed that the oligonucleotide probe hybridized exclusively to the 5.2 kb HindIII fragment in each of the three recombinant plasmids. One of these recombinant plasmids, designated pEG201, was selected for further experimentation and evalution.

It was likely that the cloned 5.2 kb HindIII fragment (corresponding to the approximately 5.0 kb HindIII fragment hybridized with the oligonucleotide probe) contained at least the $NH_2$-terminal coding region of the cryIIA gene. Presence of the cryIIA gene on the 5.2 kb fragment was verified using DNA sequencing to search for a region in the cloned 5.2 kb fragment that encoded the $NH_2$-terminus of the CryIIA protein. Since it is difficult to sequence a fragment of DNA longer than two kb it was necessary to identify a smaller fragment of DNA within the 5.2 kb fragment that would be expected to contain the cryIIA gene. Accordingly, plasmid pEG201 was digested with various restriction enzymes, the digested plasmid was electrophoresed through an agarose gel and plasmid restriction fragments were blotted from the gel to a nitrocellulose filter. Hybridization of the filter with the radioactively labelled oligonucleotide probe revealed that the probe specifically hybridized to a 1.3 kb Sau3A restriction fragment of DNA. Therefore, it was expected that the 1.3 kb fragment would contain at least the $NH_2$-terminal coding region of the cryIIA gene.

The 1.3 kb fragment was subcloned from pEG201 into the DNA sequencing vectors mp18 and mp19 (Bethesda Research Laboratories, Bethesda, Md.). DNA sequencing of the 1.3 kb fragment revealed that it contained a region of DNA that encoded the $NH_2$-terminus of the CryIIA protein. This conclusively demonstrated that the cloned 5.2 kb HindIII fragment from the donor strain HD263-1 contained the cryIIA gene. Additional DNA sequencing of the 1.3 kb fragment showed that an AccI restriction site was located 150 nucleotides upstream from the $NH_2$-terminal methionine codon of the cryIIA gene. The position of this AccI site served as a marker. It allowed the location of the cryIIA gene in the 5.2 kb fragment to be precisely determined as described below.

The location and direction of transcription of the cryIIA gene on the cloned 5.2 kb fragment was determined by digesting the 5.2 kb fragment with AccI in combination with various other restriction enzymes. The restriction fragments were electrophoresed through an agarose gel and blotted onto a nitrocellulose filter. By hybridizing the filter with the radioactively labelled cryIIA gene-specific oligonucleotide probe it was possible to determine the location and orientation of various restriction fragments on the larger 5.2 kb fragment. From this knowledge, the precise position and direction of transcription of the cryIIA gene on the 5.2 kb fragment of pEG201 was determined.

FIG. 1 shows a restriction map of plasmid pEG201. The position and direction of the ca. 2.2 kb cryIIA gene is indicated by the arrow in FIG. 1. pBR322 vector is indicated by an open boxed area. The single horizontal line denotes cloned B.t. DNA from strain HD263-1. The length of the cryIIA gene was estimated to be approximately 2.2 kb based on the estimated size (ca. 71 kDa) of the CryIIA protein.

It was estimated that all or at least most of the cryIIA gene was contained in the 2.2 kb AccI-HindIII fragment within the cloned 5.2 kb fragment (FIG. 1). Accordingly, the 2.2 kb AccI-HindIII fragment was subcloned into the sequencing vectors mp18 and mp19 and the complete sequence of the 2.2 kb fragment was determined by the dideoxy procedure of Sanger (F. Sanger, et al.), *Proc. Natl. Acad. Sci. USA,* 74, pp. 5463–5467 (1977). As expected, the 2.2 kb fragment contained an open reading frame (protein coding region) that began with the $NH_2$-terminal codons for the CryIIA protein.

Figure 3:
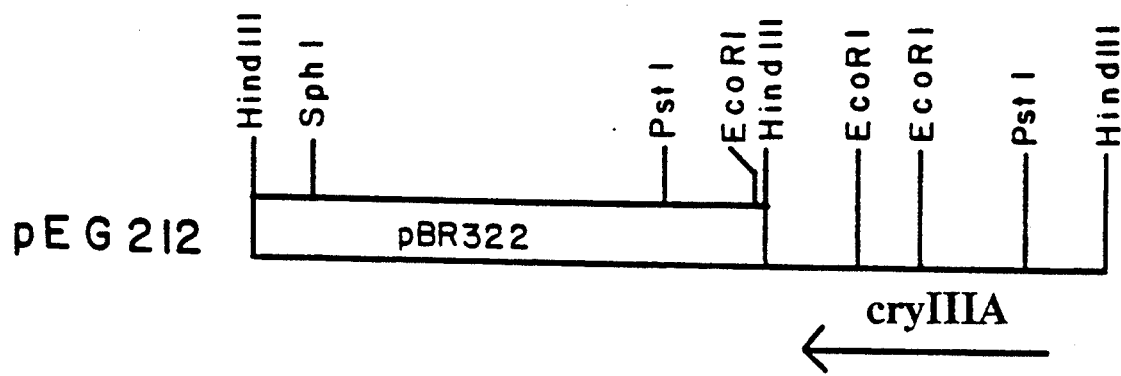
FIG. 3 is a restriction map of the recombinant plasmid pEG212 containing the cloned cryIIIA (cryC) gene which includes the promoter region as well as the coding region.
Figure 5A:
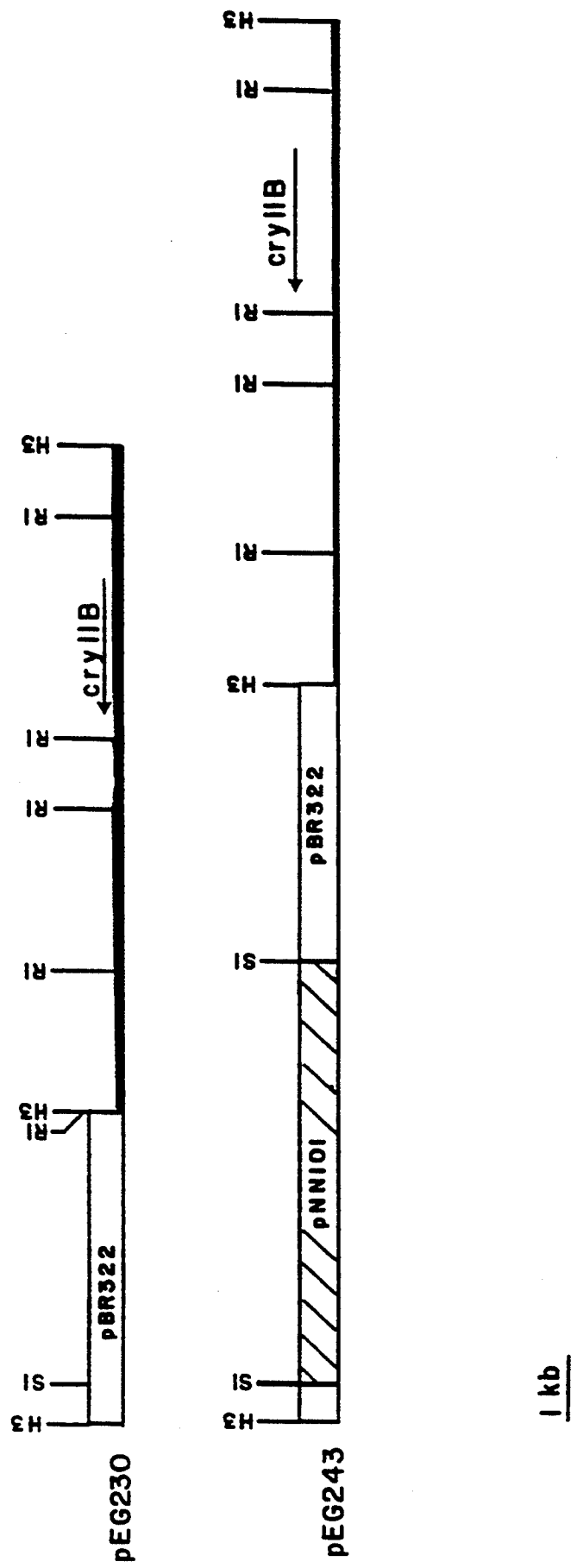
FIG. 5 comprises FIGS. 5A and 5B and illustrates restriction maps for six recombinant plasmids: pEG230 and pEG243 on FIG. 5A and pEG254, pEG256, pEG255 and pEG245 on FIG. 5B. The recombinant plasmids include cloned or subcloned fragments of DNA including nucleotide sequences containing the cryIIB gene, the cryIIIA gene and the hybrid cryIIIA-/IIB fusion gene. The arrows in the restriction maps indicate the orientation and extent of the cryIIB and cryIIIA coding regions. In each map, H3 means HindIII; R1 means EcoRI, RV means EcoRV, and S1 means SphI.
Figure 5B:
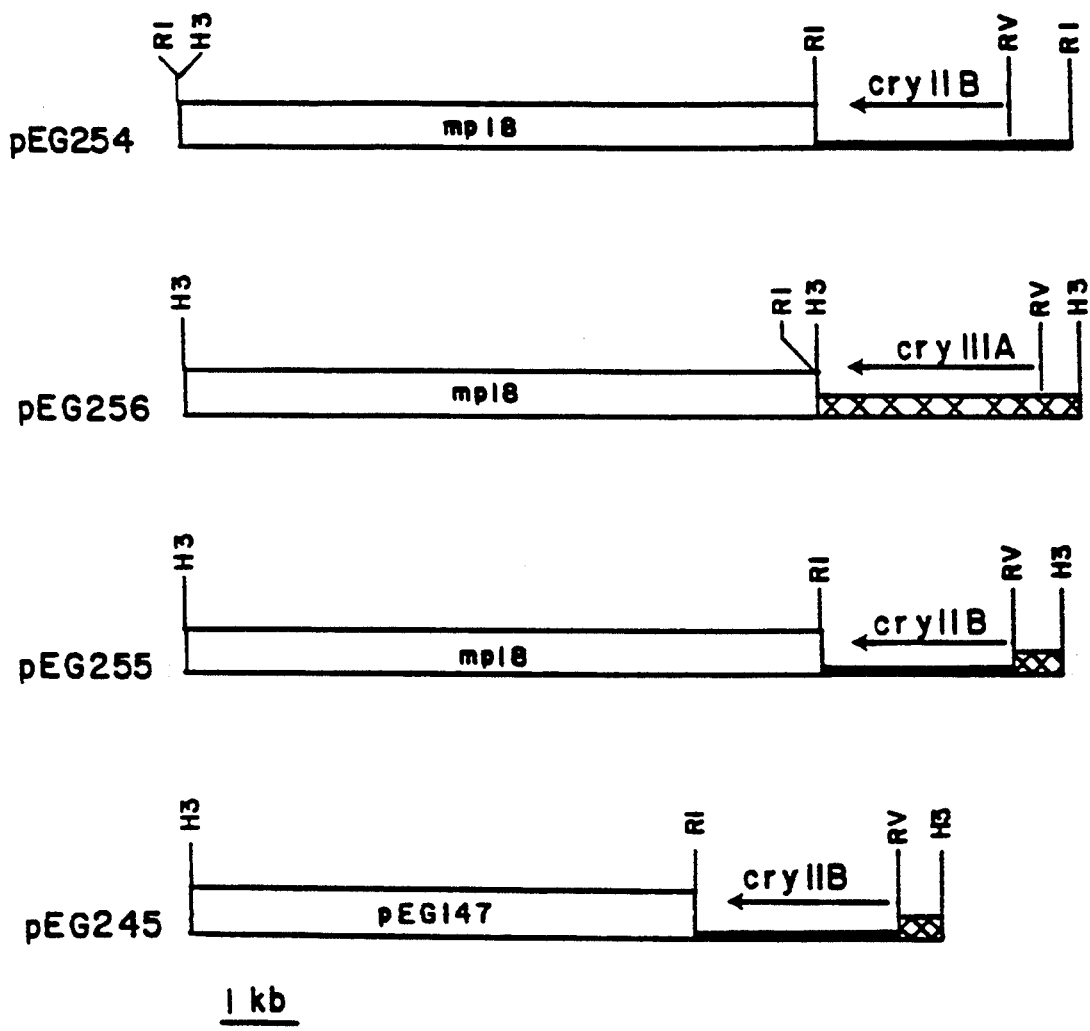

The DNA sequence of the 2.2 kb fragment, which includes the cryIIA gene, and the deduced amino acid sequence of the CryIIA protein are shown in FIG. 2 comprising FIGS. 2-1 through 2-3. FIG. 2 shows the complete DNA sequence of the 2.2 kb AccI-HindIII fragment beginning with the first nucleotide of the AccI site and ending with the last nucleotide of the HindIII site. The AccI site is located 150 nucleotides upstream from the $NH_2$-terminal methionine codon of the cryIIA gene. The size of the CryIIA protein, as deduced from the cryIIA gene sequence, was determined to be 70,860 Da.

EXAMPLE 3

Detection of CryIIA-Related Sequences

The 2.2 kb AccI-HindIII fragment containing the cryIIA gene from pEG201 was radioactively labelled and used as a probe in DNA blot hybridization experiments for HindIII-digested total DNA from the CryIIA crystal-producing strains B.t.k. HD-1 and HD-263 and B.t. var. kenyae HD-278, as well as the CryIIA-negative *B.t.* var. *israelensis* strain HD-567.

As expected, at low hybridization stringency (55° C.), the cloned cryIIA gene hybridized to 5.2 kb HindIII fragments from strains HD-263, HD-1 and HD-278. Surprisingly, the cryIIA gene also hybridized to 9.0 kb HindIII fragments from strains HD-263 and HD-1, and to a HindIII fragment of 4.4 kb from strain HD-278. The cryIIA gene failed to hybridize to any HindIII fragments from the CryIIA-negative strain HD-567. The nitrocellulose filter was rewashed at 80° C. and exposed to x-ray film. The resulting autoradiogram showed that, after the higher wash temperature, significantly less of the labelled cryIIA gene probe was bound to the 9.0 and 4.4 kb fragments than to the 5.2 kb fragment.

The fact that the 9.0 kb and 4.4 kb fragments are of a different size than the cryIIA-containing 5.2 kb fragment and the fact that the 9.0 kb and 4.4 kb fragments hybridized less strongly to the cryIIA probe than did the 5.2 kb cryIIA fragment indicate that the 9.0 kb and the 4.4 kb fragments contain genes that are related to, but different from, the cryIIA gene.

Examples 4 and 5 relate to the isolation and purification of the cryIIB gene using the cryIIA gene as a cryII-specific probe and to the expression of the cryIIB gene.

EXAMPLE 4

Cloning of the cryII$_B$ Gene to Determine the Nucleotide Sequence of the cryIIB Gene and the Amino Acid Sequence of the CryIIB Protein As indicated in Example 3, the cryIIA gene contained in the 2.2 kb AccI-HindIII fragment from B.t. strain HD-263 hybridized to HindIII fragments of 5.2 kb and approximately 9.0 kb from strain HD-1. This hybridization suggested that the 9.0 kb HindIII fragment contains a cryIIA-related gene. Size selected HindIII fragments (7 to 11 kb) of total DNA from HD-1 were ligated into pBR322 and transformed into *E. coli.* The 2.2 kb AccI-HindIII fragment containing the cryIIA gene was radioactively labeled and used as a cryII-specific probe in colony blot hybridizations. Hybridizations were carried at 65° C. in 3×SSC, 10×Denhardts' solution, 200 μg/ml heparin and 0.1% SDS.

The cryIIA gene contained in the 2.2 kb fragment hybridized to a recombinant *E. coli* colony which was designated as EG1344. EG1344 contained a plasmid (designated pEG230) comprising the vector pBR322 plus the 9.0 kb HindIII fragment as indicated in the restriction map of pEG230 in FIG. 5. The cryIIA probe specifically hybridized to a 2.9 kb EcoRI fragment within pEG230 as indicated by the arrow in the restriction map.

Plasmid pEG230 was digested with EcoRI and the resulting EcoRI fragments were size fractionated by electrophoresis through an agarose gel. A gel slice containing the 2.9 kb fragment was excised and the fragment was separated from the gel slice by electroelution. The 2.9 kb EcoRI fragment from pEG230 was ligated or subcloned into the EcoRI site of the phage vector M13mp18. The resultant recombinant phage was then used to determine the complete sequence of the cryIIB gene using the well-known Sanger dideoxy sequencing method. The 2.9 kb EcoRI fragment contained an open reading frame or protein coding sequence which was designated as the cryIIB gene of 633 codons encoding a protein of 70,749 Da.

The nucleotide sequence for the cryIIB gene and the deduced sequence of the CryIIB protein are illustrated in FIG. 6, comprising FIGS. 6-1 through 6-4. The cryIIB gene protein coding sequence began with a methionine (Met) codon and was immediately preceded by a purine-rich sequence (AGGAGG) which is believed to be a ribosome binding site. As indicated hereinbefore, the protein coding region of 1899 nucleotides of the cryIIB gene contained 89% positional identity with the protein coding region of 1899 nucleotides of the cryIIA gene. The CryIIB and CryIIA proteins each contained 633 amino acid residues having an 88% positional identity.

EXAMPLE 5

Expression of the cryIIB Gene

Several experiments were conducted to determine the production of the CryIIB protein by the cryIIB gene.

The following Table 2 summarizes the relevant characteristics of the strains used in these experiments.

TABLE 2

| Bacterial strains | | |
|---|---|---|
| Strain | Genotype | Toxin Genes |
| *Escherichia coli* | | |
| HB101 | (plasmid recipient) | none |
| EG1339 | HB101(pEG220) | none |
| EG1344 | HB101(pEG230) | cryIIB |
| EG7208 | HB101(pEG245) | cryIIIA/IIB |
| *Bacillus thuringiensis* | | |
| HD-1 | Wild-type | cryIIA, cryIIB |
| HD-263 | Wild-type | cryIIA, cryIIB |
| HD-122 | Wild-type | cryIIB |
| HD73-26 | (plasmid recipient) | none |
| EG1329 | HD73-26(pEG221) | cryIIA |
| EG7211 | HD73-26(pEG220) | none |
| EG7203 | HD73-26(pEG243) | cryIIB |
| EG7210 | HD73-26(pEG245) | cryIIIA/IIB |

B.t. strains HD-1, HD-263 and HD-122 were obtained from USDA, Cotton Insect Research Unit, Brownsville, Tex. 78520, as was B.t. strain HD-73, the precursor to HD73-26.

B.t. crystal-negative strain HD73-26 was derived by growing strain HD-73 at a temperature of about 42° C. for about 1 day. One colony, designated HD73-26, was found which no longer contained large plasmids and that no longer produced crystal proteins.

B.t. strain EG1329 is HD73-26 (pEG221) carrying the cryIIA gene. pEG221 is tetracycline resistant (Tc$^r$), chloramphenicol resistant (Cm$^r$), and ampicillin resistant (Ap$^r$), and comprises a 4.0 kb BamHI-HindIII fragment containing the cryIIA gene from HD-263 carried on the *E. coli-Bacillus* shuttle vector pEG220. pEG220 ($Tc^r$, $Cm^r$, $Ap^r$) comprises the Bacillus vector pNN101 ($Tc^r$, $Cm^r$) ligated into the SphI site of the *E. coli* vector pBR322 ($Tc^r$, $Ap^r$).

*E. coli* strain EG1339 is HB101 harboring shuttle vector pEG220.

*E. coli* strain EG1344 is HB101 harboring plasmid pEG230, a restriction map of which is illustrated in FIG. 5.

B.t. strain EG7203 is strain HD73-26 harboring plasmid pEG243, a restriction map of which is illustrated in FIG. 5.

*E. coli* strain EG7208 is HB101 harboring plasmid pEG245, a restriction map of which is illustrated in FIG. 5. Plasmid pEG245 comprises the 2.6 kb HindIII-EcoRI fragment containing cryIIIA/IIB inserted into shuttle vector pEG147 ($Tc^r$, $Ap^r$), which was constructed by ligating the 3.1 kb EcoRI fragment containing the origin of replication and $Tc^r$ determinant from Bacillus plasmid pBC16($Tc^r$) into the SspI site of *E. coli* plasmid pUC18($Ap^r$).

B.t. strain EG7210 is HD73-26 harboring plasmid pEG245 a restriction map of which is illustrated in FIG. 5.

B.t. strain EG7211 is HD73-26 harboring shuttle vector pEG220.

*E. coli* strains were grown in LB medium (1% Difco tryptone, 0.5% Difco yeast extract, 0.5% NaCl, pH 7.0) at 37° C. B.t. strains were grown in M55 medium (0.15% (w/v) potato dextrose broth, 0.27% (w/v) nutrient broth, 0.01% L-methionine, 29 mM $K_2HPO_4$, 37 mM $KH_2PO_4$, 1 mM citric acid, 150 mM NaCl, 5 mM $(NH_4)_2SO_4$, 500 $\mu$M $CaCl_2$, 330 $\mu$M $MgCl_2$, and 1 $\mu$M each of $ZnCl_2$, $CuCl_2$, $Na_2MbO_4$) at 30° C.

The culturing of the cells and the size fractionation of the proteins were based on the following methods. Cell cultures were grown for 48–72 hours in the media and at the temperatures set forth above to stationary phase (*E. coli*) or to sporulation (B.t.). *E. coli* cells or B.t. spores plus crystals were harvested by centrifugation, washed twice with TE (10 mM Tris.HCl pH 7.5, 1 mM EDTA), and suspended in TE (100 mg wet weight, per ml). Ten to 30 $\mu$l of the cell/crystal suspension were added to 90 $\mu$l of pre-heated loading buffer (0.13M Tris pH 6.8, 2% SDS, 5% 2-mercaptoethanol, 0.05% bromphenol blue, 20% glycerol), incubated at 95° C. for 7 min and vortexed 20 sec. 10 $\mu$l of the mix were loaded onto a 10% polyacrylamide slab gel containing SDS for size fractionation of proteins. After SDS-PAGE, proteins were quantified by densitometer tracings of Coomassie stained polyacrylamide gels. Renografin purified CryIIA crystal protein, quantified by the bicinchoninic acid kit assay method according to the manufacturer (Pierce Chemicals, Rockford, Ill.), were used as a standard on Coomassie stained SDS-polyacrylamide gels.

Microscopic examination of *E. coli* EG1344 cells (carrying cryIIB on PEG230) grown to stationary phase as described above revealed that the cells did not produce any observable crystal proteins. EG1344 cell lysates were fractionated by SDS-PAGE and total cell protein was visualized by Coomassie staining. EG1344 cells (FIG. 7A, lane 2) appeared to contain the same complement of proteins as an isogenic *E. coli* Cry− control strain (EG1339) (FIG. 7A, lane 1) harboring only the plasmid vector pEG220(Cry−). Polyclonal antibodies raised to the CryIIA protein were used in an attempt to detect the CryIIB protein.

Polyclonal antibodies were raised in mice that had been immunized subcutaneously with Renografin density gradient purified-CryIIA crystals obtained from B.t.k. strain HD-1, and that had been boosted intramuscularly at 5 weeks with gel-purified CryIIA protein. Mouse immunoglobulins were isolated from high titer antisera by protein A-Sepharose affinity chromatography. SDS-PAGE/immunoblot (Western) analysis was conducted using an alkaline phosphatase-linked rabbit anti-mouse IgG second antibody probe.

Anti-CryIIA antibodies failed to react with any CryIIB-sized protein in Western blots of EG1344 cell lysates (FIG. 7B, lane 2). These experiments revealed that cryIIB-containing *E. coli* cells did not produce the CryIIB protein. The failure to detect the CryIIB protein in EG1344 cells was not unexpected in view of previous work with the cloned cryIIA gene (Donovan (1)), as well as with the cloned cryIIIA gene (Donovan (3)), which showed that *E. coli* cells harboring these cloned genes produced very little, if any, of the respective crystal proteins.

To measure the expression in B.t. of the cloned cryIIB gene, plasmid pEG243 was constructed by inserting the Bacillus vector pNN101 ($Tc^r$, $Cm^r$) into the unique SphI site of the *E. coli* plasmid pEG230 (carrying cryIIB). A restriction map of pEG243 is illustrated in FIG. 5. pEG243 is capable of replicating in both *E. coli* and B.t., and is therefore a shuttle vector. The 9.0 kb HindIII fragment from HD-1 that is cloned in pEG243 contains the complete cryIIB coding region plus approximately 2 kb of cryIIB-upstream DNA and approximately 5 kb of cryIIB-downstream DNA. The method of cell electroporation was used to transform pEG243 into the crystal-negative B.t. strain HD73-26 yielding strain EG7203.

Microscopic examination after culturing showed that sporulated cultures of B.t. EG7203 cells (carrying cryIIB on pEG243) did not contain any observable crystal proteins. SDS-PAGE fractionation of total proteins from EG7203 cells (FIG. 7A, lane 5) showed that these cells contained an apparently identical complement of proteins as an isogenic Cry− control strain of B.t. (EG7211) (FIG. 7A, lane 4) that harbored only the vector pEG220(Cry−). Western blot analysis showed that anti-CryIIA antibodies reacted with a CryIIB-sized protein of approximately 70 kDa that was present in very minor amounts in EG7203 cells, although the reacting protein band is not visible in the photograph of FIG. 7B (lane 5). This reacting band was not observed in the control strain EG7211(Cry−). Based on previous findings with cloned crystal protein genes, it was expected that sporulated cultures of EG7203 would contain significantly more of the CryIIB protein than was actually found.

It was possible that some regulatory function required for the efficient expression of the cryIIB gene was lost during cloning of the gene and, if so, this could explain the unexpectedly low level of CryIIB protein produced by EG7203 cells. In view of this, the production of CryIIB protein by a wild-type B.t. strain harboring the cryIIB gene on a native plasmid was measured. DNA blot hybridization analysis showed that strains HD-1 and HD-263 harbored the cryIIA and cryIIB genes on a native 110 MDa plasmid. The amount of CryIIB protein produced by HD-1 and HD-263 could not be measured because of the production of the CryIIA protein by these strains which would mask the presence, if any, of the CryIIB protein.

One wild-type B.t. strain was found (HD-122) which contained a single cryIIA-hybridizing HindIII fragment of 9.0 kb, indicating that this strain harbored the cryIIB gene but not the cryIIA gene. DNA blot hybridization analysis showed that HD-122 contained the cryIIB gene on a native 110 MDa plasmid. Microscopic examination of sporulated cultures of HD-122 revealed that the cells produced only bipyramidal crystals characteristic of CryI-type of crystal proteins. SDS-PAGE analysis of total protein from sporulated cultures of HD-122 revealed only one significant protein band. This band was approximately 130 kDa, a size typical of CryI-type of crystal proteins (FIG. 7A, lane 7). In Western blot analysis, anti-CryIIA antibodies failed to react with any protein from HD-122 cells (FIG. 7B, lane 7). These experiments showed that HD-122 produced very little, if any of the CryIIB protein and suggested that the unexpectedly low level of production of the CryIIB protein by recombinant B.t. cells harboring the cloned cryIIB gene was not due to an artifact of cloning the cryIIB gene.

In view of the experiments of Example 5, other experiments were devised to determine if the CryIIB protein could be produced in greater quantities by attaching a foreign promoter to the cryIIB gene in place of the native promoter. One of the promoters investigated was that contained in the cryIIIA gene from B.t. strain EG2158.

Examples 6 and 7 relate to B.t. strain EG2158 and the isolation and purification of the cryIIIA gene and the encoded CryIIIA protein.

EXAMPLE 6

Culturing B.t. Strain EG2158 and Purification of the CryIIIA Protein, Determination of NH$_2$-Terminal Amino Acid Sequence of the CryIIIA Protein and Preparation of Oligonucleotide Probe The cryIIIA gene (formerly cryC) encoding the CryIIIA protein (formerly CryC protein) was isolated from B.t. strain EG2158 as described in Donovan (3). Briefly, EG2158 cells were grown until sporulation occurred and crystal proteins were produced. The spores plus crystal proteins were harvested by centrifugation and the crystal proteins were solubilized in a buffer of SDS plus B-mercaptoethanol. The solubilized crystal proteins were size fractionated on an SDS-polyacrylamide gel and the CryIIIA protein was identified by its property of being the major visible protein band in the gel. Judging from its distance of migration on the SDS-polyacrylamide gel, the CryIIIA protein was estimated to be approximately 68 kDa in size. A gel slice containing the fractionated CryIIIA protein was cut out. The CryIIIA protein was purified by separating the protein from the gel slice by electroelution. The purified CryIIIA protein was sent to an outside laboratory for the determination of its NH$_2$-terminal amino acid sequence.

The NH$_2$-terminal sequence was determined to be NH$_2$-As$_p$ Glu Ala Leu Thr Ser Ser Thr Asp Lys Asp Val Ile Gln Lys Gly Ile Ser Val Val Ile Asp Leu Leu-COOH. The sequence did not begin with the expected Met amino acid. It was subsequently found that the protein was processed from a larger precursor which did contain the NH$_2$-terminal Met as explained below. The amino acid sequence from amino acids (Asp) to amino acid 22 (Asp) was used to design an oligonucleotide probe.

The sequence of the probe was 5'-GAT GAA GCA TTA ACA TCA TCA ACA GAT AAA GAT GTA ATT CAA AAA GGA ATT TCA GTA GTA ATT GA-3'.

EXAMPLE 7

Cloning of the cryIIIA Gene and Determination of the Nucleotide Sequence of the cryIIIA Gene and Amino Acid Sequence of the CryIIIA Protein The probe was used to isolate the cryIIIA gene by colony hybridization as follows. A plasmid library was constructed in E. coli cells. The plasmid library comprised HindIII fragments from total DNA from strain EG2158 ligated into the HindIII site of the plasmid vector pBR322. The oligonucleotide probe was radioactively labeled and was used in a hybridization experiment with E. coli cells containing the plasmid library. The probe specifically hybridized to one E. coli colony containing a plasmid (designated pEG212) that comprised the plasmid vector pBR322 plus a 2.9 kb HindIII DNA fragment inserted into the HindIII site of the pBR322 vector. A restriction map of plasmid pEG212 is shown in FIG. 3.

The oligonucleotide probe specifically hybridized to the 2.9 kb HindIII fragment within plasmid pEG212, thereby indicating that the cryIIIA gene was located on the 2.9 kb fragment. Plasmid pEG212 was digested with HindIII. The 2.9 kb fragment was purified by gel electrophoresis and the fragment was ligated into the HindIII sites of the phage vectors M13mp18 and M13mp19. These recombinant phage vectors containing the HindIII fragment were then used to determine the complete sequence of the 2.9 kb fragment using the Sanger dideoxy sequencing method. The complete nucleotide sequence of the 2.9 kb fragment is shown in FIG. 4, comprising FIGS. 4-1 through 4-4. The 2.9 kb fragment contained an open reading frame which began with the sequence Met Asn Pro. Immediately upstream from Met was the sequence GGAGGA that is believed to be a ribosome binding site. 54 codons downstream from Met in the open reading frame is the sequence Thr Glu Ala Leu Asp Ser Ser Thr Thr Lys. This sequence closely matched the sequence that had been previously determined for the 68 kDa CryIIIA protein. Therefore, the open reading frame is the cryIIIA gene.

The deduced amino acid sequence of the CryIIIA protein is shown beneath the nucleotide sequence of the cryIIIA gene in FIGS. 4-1 through 4-4. The CryIIIA protein contains 644 residues and has a deduced molecular weight of 73,116 Da. The NH$_2$-terminal sequence of the purified CryIIIA protein, as determined by the outside lab, began 54 codons downstream from the NH$_2$-terminus of the CryIIIA protein as deduced from the sequence of the cryIIIA gene. It is believed that this discrepancy in the beginning of the NH$_2$-terminal sequence is due to bacterial proteases which cleaved off 54 amino acids from the NH$_2$-terminus of the CryIIIA protein during purification of the protein.

The following example relates to the recombinant hybrid cryIIIA/IIB fusion gene and the expression of it resulting in enhanced production of the CryIIB protein.

EXAMPLE 8

Construction and Expression of the Recombinant Hybrid cryIIIn/IIB Fusion Gene

Plasmid pEG212 (FIG. 3) contains the coleopteran toxic cryIIIA gene as part of a 2.9 kb HindIII fragment from B.t. strain EG2158 in the plasmid vector pBR322. The sequence of the 2.9 kb fragment has been determined as set forth in Example 7. The 2.9 kb fragment consists of the cryIIIA coding region plus ca. 0.5 kb of DNA upstream from the cryIIIA translation initiation site. The nucleotide sequence of the 0.5 kb cryIIIA upstream region is shown in FIG. 4-1, extending from nucleotide 1 to nucleotide 549. Sekar et al. (1987) has shown that the cryIIIA gene transcription start site is 130 nucleotides upstream from the cryIIIA methionine (Met) translation initiation codon and within the 0.5 kb cryIIIA upstream region.

A recombinant hybrid cryIIIA/IIB fusion gene was created by oligonucleotide-directed mutagenesis using the Biorad Muta-gene Kit according to the manufacturer's procedure and based on the well-known methods of M. J. Zoller et al. *Methods Enzymology,* 154, pp. 329–350 (1987), and T. A. Kunkel et al. *Methods Enzymology,* 154, pp. 367–382 (1987). Oligonucleotide-directed mutagenesis involves the hybridization of a synthetic oligonucleotide to a specific site on the sequence of the gene to be mutated. The gene sequence which is to be mutated is complementary to the oligonucleotide except for a few non-complementary nucleotides. These non-complementary nucleotides will become a part of the new, mutated gene sequence. The oligonucleotide is hybridized to the complementary site on the gene. Once hybridization has occurred, the oligonucleotide can serve as a primer for the enzyme DNA polymerase. DNA polymerase uses the oligonucleotide primer plus the sequence of the original gene to synthesize a new gene. The new gene is identical to the original gene with the exception of the few non-complementary nucleotides that were present in the oligonucleotide primer. Thus, the non-complementary nucleotides of the oligonucleotide become the mutant nucleotides that are present in the new gene sequence.

Using this process, the cryIIB gene sequence 5'TATTAC (nucleotides 844 to 849 shown in FIG. 6-1) was mutated to 5'GATATC (EcoRV recognition site) by use of the synthetic oligonucleotide 5'AATTTTAATAGATATCTTAATATTTA (the non-complementary nucleotides are underlined) and the cryIIIA sequence 5'GATAAG (nucleotides 547 to 552 shown in FIG. 4-1) was changed to 5'GATATC (EcoRV site) by use of the synthetic oligonucleotide 5'TATGTATTATGATATCAAAGGGAGGA (the non-complementary nucleotides are underlined).

The resulting 2.5 kb EcoRV-EcoR1 cryIIB fragment was subcloned from pEG254 (FIG. 5) into the EcoRV-EcoRI sites of pEG256 (FIG. 5), yielding plasmid pEG255 (FIG. 5). pEG255 comprises the vector M13mp18 plus the 0.5 kb cryIIIA upstream DNA (nucleotides 1 to 549 of cryIIIA) fused to the cryIIB coding region (nucleotides 847 to 2924 containing the complete cryIIB protein coding region plus 27 nucleotides upstream from the cryIIB translation initiation site and 149 nucleotides downstream from the cryIIB translation termination site). Sequencing of pEG255 verified that the 2.6 kb HindIII-EcoRI cryIIIA/IIB fragment had the expected sequence.

The 2.6 kb HindIII-EcoRI cryIIIA/IIB fragment was subcloned into the HindIII-EcoRI sites of the Bacillus-*E. coli* shuttle vector pEG147, yielding plasmid pEG245 (FIG. 5). Shuttle vector pEG147 ($Tc^r$, $Ap^r$) was constructed by ligating the 3.1 kb EcoRI fragment containing the origin of replication and tetracycline resistance determinant from the Bacillus plasmid pBC16($Tc^r$) into the SspI site of the *E. coli* plasmid pUC18($Ap^r$). pEG245 was transformed into the crystal-negative B.t. strain HD73-26, yielding strain EG7210.

Strain EG7210 was cultured in M55 medium as explained above to sporulation. Microscopic examination showed that sporulated cultures of EG7210 cells containing the fusion gene cryIIIA/IIB produced phase-bright inclusions characteristic of crystal proteins. The crystal-like inclusions were observed inside unlysed cells and also free in the growth medium.

Fractionation of proteins by SDS-PAGE showed that EG7210 cells produced significant amounts of a protein of approximately 70 kDa, (FIG. 7A, lane 6), a size corresponding to that expected for the CryIIB protein. This protein also reacted with anti-CryIIA antibodies as determined by Western blot analysis (FIG. 7B, lane 6). The CryIIB protein accounted for approximately 1–2% of the wet weight of EG7210 cells as determined from densitometer tracings of Coomassie stained SDS-polyacrylamide gels.

As expected, no crystal protein-like inclusions were observed with *E. coli* cells (strain EG7208) harboring pEG245 (carrying the cryIIIA/IIB fusion gene) and the cells failed to produce detectable levels of the CryIIB protein as measured by either Coomassie staining of SDS-polyacrylamide gels or Western blot analysis (FIGS. 7A and B, lane 3).

Expression of the cryIIB gene was increased by at least an order of magnitude when the DNA fragment containing the cryIIIA promoter (but lacking the the cryIIIA ribosome binding site) was fused to the cryIIB ribosome binding site plus the CryIIB protein coding region. Thus, by comparing FIG. 7, lane 6 (B.t. strain EG7210 carrying the cryIIIA/IIB fusion gene) with lane 5 (B.t. strain EG7203 carrying the cryIIB gene), it can be seen that with the present invention, the recombinant cryIIIA/IIB fusion gene results in substantially greater expression and production of the CryIIB protein than the cryIIB gene with its native promoter.

Example 9 relates to experiments to determine the insecticidal activity of the CryIIB protein versus the CryIIA protein.

EXAMPLE 9

Insecticidal Activities of the CryIIB Protein and the CryIIA Protein

B.t. cells containing the cryIIIA/IIB fusion gene (strain EG7210) and the cryIIA gene (strain EG1329) were grown in sporulation medium containing 5 μg/ml tetracycline. After 72 hours growth at 25° C., spores plus crystal proteins were harvested, washed twice with TE, suspended in TE, and serially diluted. Activity against lepidopteran larvae was determined by application of 100 μl of each spore/crystal dilution to 3 ml of an agar base artificial diet in a plastic feeding cup (600 mm square surface area). One neonate larva was placed in each cup, and mortality was scored after 7 days. Activity against dipteran larvae (mosquitos) was determined by placing *Aedes aegypti* fourth instar larvae in 50 ml of deionized water containing serial dilutions of the bacterial spore/crystal protein suspensions, and mortality was scored after 72 hours. $LD_{50}$ values were determined by probit analysis as described by R. Daum, *Bull. Entomol. Soc. Am.*, 16, pp. 10-15 (1970), using a 6-dose testing procedure with at least 40 larvae at each dose. The results are summarized in the following Table 3:

TABLE 3

Insect Toxicity of The CryIIB and CryIIA Proteins

| Protein | L. dispar | H. virescens | T. ni | H. zea | O. nubilalis | A. aegypti |
|---|---|---|---|---|---|---|
| CryIIB | 56;33[1] | 124 | 150;135 | 378;349 | 623;241, | >20 |
| CryIIA | 19;13 | 93 | 166;98 | 619;742 | 115;33 | 1-5 |

[1]For L.d., H.v., T.n., H.z. and O.n., the numbers are $LD_{50}$ values in nanograms of CryIIB protein or CryIIA protein per diet cup as determined from a single bioassay (H.v.) or from duplicate bioassays (L.d., T.n., H.z. and O.n.). For *A. aegypti*, the numbers are $LD_{50}$ values in micrograms of CryIIB or CryIIA protein per ml deionized water.

As indicated in Table 3, the CryIIB protein was approximately one seventh and one third as toxic as the CryIIA protein against the lepidopteran species *Ostrinia nublilalis* (European corn borer) and *Lymantria dispar* (gypsy moth), respectively. The CryIIB protein was roughly equally as toxic as the CryIIA protein against the lepidopteran species *Heliothis virescens* (tobacco budworm) and *Trichoplusia ni* (cabbage looper). Significantly, the CryIIB protein was twice as toxic as the CryIIA protein against the lepidopteran *Heliothis zea* (corn earworm). The two proteins exhibited a major difference in their toxicities to the dipteran insect *Aedes aegypti*. Unlike the mosquito-toxic CryIIA protein, the CryIIB protein was not toxic to *A. aegypti*.

The present invention may be embodied in other specific forms without departing from the spirit or essential attributes thereof and, accordingly, reference should be made to the appended claims, rather than to the foregoing specification as indicating the scope of the invention.

I claim:

1. A CryIIB protein which is insecticidal against lepidopteran insects, the protein having an amino acid sequence as shown in FIG. 6 at positions 874 to 2775.

2. A CryIIB protein produced by a cryIIB gene, having a nucleotide base sequence as shown in FIG. 6 extending from positions 874 to 2775.

3. An insecticidal composition active against lepidopteran insects comprising an insecticidally effective amount of the protein of any one of claims 1 or 2 and an agriculturally acceptable carrier.

4. The insecticidal composition of claim 3 wherein the protein is contained in a *Bacillus thuringiensis* bacterium.

5. A method of controlling lepidopteran insects comprising applying to a host plant for such insects an insecticidally effective amount of the protein of any one of claims 1 or 2.

6. The method of claim 5 wherein the protein is contained in a *Bacillus thuringiensis* bacterium.

* * * * *